(12) United States Patent  
Molnar et al.

(10) Patent No.: US 8,530,811 B2  
(45) Date of Patent: Sep. 10, 2013

(54) LIGHT FIELD IMAGE SENSOR, METHOD AND APPLICATIONS

(75) Inventors: Alyosha Molnar, Ithaca, NY (US); Albert Wang, Ithaca, NY (US)

(73) Assignee: Cornell University, Ithaca, NY (US)

( * ) Notice: Subject to any disclaimer, the term of this patent is extended or adjusted under 35 U.S.C. 154(b) by 332 days.

(21) Appl. No.: 13/055,566

(22) PCT Filed: Jul. 24, 2009

(86) PCT No.: PCT/US2009/051660  
§ 371 (c)(1), (2), (4) Date: Apr. 6, 2011

(87) PCT Pub. No.: WO2010/044943  
PCT Pub. Date: Apr. 22, 2010

(65) Prior Publication Data  
US 2011/0174998 A1   Jul. 21, 2011

Related U.S. Application Data

(60) Provisional application No. 61/083,688, filed on Jul. 25, 2008.

(51) Int. Cl.  
*G02B 27/42* (2006.01)

(52) U.S. Cl.  
USPC .................. 250/206.1; 250/237 G; 250/216; 250/208.1

(58) Field of Classification Search  
USPC .................. 250/208.1, 216, 206.1, 237 G  
See application file for complete search history.

(56) References Cited

U.S. PATENT DOCUMENTS

| | | | | |
|---|---|---|---|---|
| 4,915,463 A * | 4/1990 | Barbee, Jr. | | 359/360 |
| 7,211,820 B2 * | 5/2007 | Gunapala et al. | | 257/21 |
| 7,800,823 B2 * | 9/2010 | Perkins | | 359/485.05 |

FOREIGN PATENT DOCUMENTS

| | | |
|---|---|---|
| JP | 2004279191 | 10/2004 |
| JP | 2005061981 | 3/2005 |
| KR | 20070012267 | 1/2007 |

* cited by examiner

*Primary Examiner* — Tony Ko  
(74) *Attorney, Agent, or Firm* — William Greener; Bond, Schoeneck & King, PLLC

(57) ABSTRACT

An angle-sensitive pixel (ASP) device that uses the Talbot effect to detect the local intensity and incident angle of light includes two local diffraction gratings stacked above a photodiode. When illuminated by a plane wave, the upper grating generates a self-image at a selected Talbot depth. The second grating, placed at this depth, blocks or passes light depending upon incident angle. Several such structures, tuned to different incident angles, are sufficient to extract local incident angle and intensity. Arrays of such structures are sufficient to localize light sources in three dimensions without any additional optics.

29 Claims, 22 Drawing Sheets

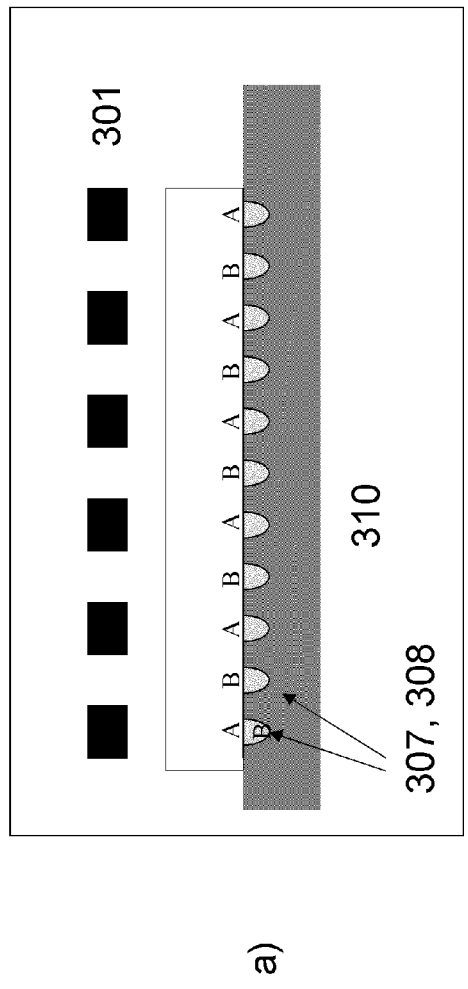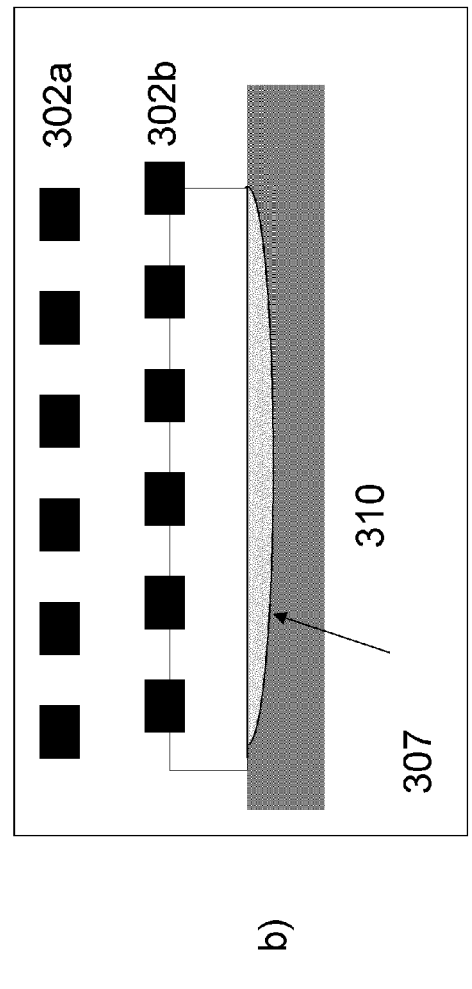
FIG 3a
FIG 4

LIGHT FIELD IMAGE SENSOR, METHOD AND APPLICATIONS

RELATED APPLICATION DATA

The instant application claims priority to U.S. Provisional application Ser. No. 61/083,688 filed on Jul. 25, 2008, the subject matter of which is incorporated herein by reference in its entirety.

FEDERALLY SPONSORED RESEARCH

Not applicable.

BACKGROUND

1. Field of the Invention

Embodiments of the invention are generally directed to the field of light field and light field image detection. More particularly, embodiments of the invention are directed to a lens-less, angle-sensitive pixel (ASP) device and to a lens-less light field image detector comprised of two or more of the lens-less ASP devices that can measure the intensity and direction angle of a light field to provide an image of the light field. Embodiments of the invention further include, without limitation, a pseudo-3-D CMOS, ASP imaging device, imaging methods associated with said device embodiments, and applications thereof.

2. Related Art Discussion

Conventional imaging uses a large array of light sensors to create a map of light intensity at an image plane. However, this intensity map fails to capture incident angle, polarization angle, and other properties of light rays passing through the image plane. A complete description of these additional parameters defines the light field or, "flow" of light, at the image plane.

Michael Faraday first proposed the concept of light as a field in the mid 1800's. This concept was expanded by the theory of a "light field" in three-dimensional space. At a given point, the light field is defined by the infinite collection of vectors that represent the light arriving at the point from all angles. The light field can be formally defined by a "plenoptic function" of multiple variables. The plenoptic function parameterizes the light rays passing through all space in terms of intensity, I, which is dependent on position in space (x, y, z), direction ($\theta$, $\phi$), wavelength ($\lambda$), time (t), and polarization angle (p). Hence, I(x, y, z, $\theta$, $\phi$, $\lambda$, t, p) is the complete representation of a visual scene and contains all possible views of the scene.

Measuring the plenoptic function would require an observer to be able to determine the intensity of every ray, for every wavelength, at all instants in time and at every point in space. Clearly, perfect determination of the plenoptic function for any practical scene is impossible. However, a number of techniques collectively known as light-field imaging have been devised that can record aspects of the plenoptic function beyond simple intensity at a plane. One reported method is to use an array of pinhole cameras, where each camera captures the incident angle-dependent intensity I($\theta$, $\phi$) at a particular location, ($x_0$, $y_0$). Cameras at different positions ($x_i$, $y_i$) capture a slice of the plenoptic function, I(x, y, $\theta$, $\phi$). Arrays of conventional cameras can also be used, as can camera scanning, or multiple masks. Small-scale solutions have used micro-lenses to emulate camera arrays. However, all of these approaches require a significant number of parallel or moveable optical components to capture information about the light field beyond a simple intensity map.

Recording information about the light field of a scene provides a more complete description of that scene than a conventional photograph or movie, and is useful for a number of applications. The light field allows prediction of illumination patterns on a surface given known sources and the three-dimensional reconstruction of scenes (e.g., "light-field rendering" or "three-dimensional shape approximation"). FIGS. 1a, 1b show how one aspect of the light field, e.g., incident angle, can be used to localize a light source in three-dimensional space. Capturing the light field also permits construction of images with an arbitrary focal plane and aperture. This capability is useful in both photography and in microscopy for obtaining multiple focal planes without moving optics.

A wide variety of applications require information about the three-dimensional structure of microscale samples. Direct capture of this information using commodity semiconductor chips with no additional hardware would reduce the size and cost of many instruments and assays by orders of magnitude. Existing solid-state image sensors employ large arrays of photosensitive pixels that capture an intensity map of incident light, but no angle information. In typical imaging applications, a lens is required to ensure that the intensity map represents some object of interest. Without a lens, one must rely purely on the information contained in the light rays striking the image sensor. If a sample is placed sufficiently close to the image sensor and illuminated, the resulting intensity map will typically contain some blurred two-dimensional spatial information. Three-dimensional information is completely lost. Information contained in the incident angle of light rays is of interest because it contains further recoverable spatial information.

To date, macroscopic angle-detectors have been demonstrated in unmodified integrated circuit technology. Pixel-scale angle-sensitive structures have been demonstrated on chip but require post-assembled arrays of microlenses, which significantly increase cost and complexity over the manufacture and use of standard imagers.

Another reported technique involves silicon-on-insulator (SOI) structures utilizing regions of metal that are large relative to the wavelength of the light to generate a shadow on an underlying photodiode. This approach has been reportedly used to perform a single angle measurement but is not well suited to deployment in imager arrays.

The inventors recognize that solutions and improvements to the shortcomings and challenges in the prior art are necessary and would be beneficial. More specifically, in contrast to other approaches that require multiple lenses and/or moving parts, devices that are monolithic, require no optical components aside from the sensor itself, and which can be manufactured in a standard planar microfabrication process (e.g., CMOS) would be advantageous in the art. The embodiments of the invention disclosed and claimed herein successfully address these matters and achieve these goals.

SUMMARY

Embodiments of the invention are directed to apparatus and methods for measuring a light field at a given image plane. Pixel and detector devices disclosed herein are sensitive to both the intensity and the incident angle of incident light from an object scene. The disclosed apparatus and methods utilize the Talbot effect of periodic light diffracting structures to characterize incident light by its magnitude and direction. In certain aspects, local, micron-scale diffraction gratings at each of a large number of sensor sites are used to capture this information. To distinguish certain of these devices from the typical pixels of digital image sensors, we refer to them herein as "angle-sensitive pixels" (ASPs).

An embodiment of the invention is an angle-sensitive pixel device manufactured entirely in a standard CMOS fabrication process. In a non-limiting aspect, the ASP device includes a device support structure; a first periodic, light diffracting structure having a period, $p_1$, disposed in or on a top surface of the support structure; a second periodic structure having a period, $p_2$, oriented parallel to the first periodic structure and disposed in the support structure at a selected distance below the first periodic, light diffracting structure. As used herein, m, n are positive integers, $\lambda$ is the wavelength of a monochromatic, plane, incident wavefront on the first periodic, light diffracting structure, and $p_1$ is equal to or greater than $\lambda$. In an aspect, $p_1$ is equal to $p_2$. According to an aspect, the second periodic structure further includes at least two sets of at least two interleaved diffusion-type diodes, which could be finger diodes. The sets of diodes are, respectively, laterally displaced from the first periodic, light diffracting structure by a distance $np_1/m$, where n can have the values 0, 1, 2, 3, 4, 5, 6, 7, 8 and m can have the values 2, 3, 4, 8. The sets of interleaved diodes are disposed at a selected distance, $z_{T1}=(m_1/n_1)(2p_1^2/\lambda)$, below the first periodic, light diffracting structure and the second periodic structure.

An embodied micron-scale device requires both a periodic diffracting structure to generate Talbot self-images and a structure for analyzing these self-images. By sizing the entire device to fit within an area of at most tens of microns on a side, spatial resolution may be achieved that is comparable with existing image sensors. In an illustrative aspect, the periodic diffracting structure will have several periods within this area to produce an operable periodic self-image. Thus the diffracting structure may have a period of only a few wavelengths. Contemporary planar photolithography techniques can easily achieve the resolution required to generate appropriate diffracting structures. Numerical modeling and simulation can accurately predict behavior for finite gratings built on a single-micron scale.

According to a general embodiment, the structure for analyzing the self-images generated by the periodic diffracting structure may be an integrated light detector; for example, at least two, periodic, interleaved sets of at least two diffusion-type diodes as are well known in the art. According to further embodiments described herein below, the structure for analyzing the self-images may be one or more layers of periodic structures followed by a sensor in the form of at least two, periodic, interleaved sets of diffusion-type diodes, one or more single, large, well-type diodes known in the art, or a combination of the interleaved diffusion diodes disposed (and partially enclosed) in the one or more single, large, well-type diodes. The one or more layers of periodic structures may or may not be arranged co-perpendicularly.

An embodiment of the invention is a lens-less, angle-sensitive pixel (ASP) device that includes a device support structure; a first periodic, light diffracting structure having a period, $p_1$, disposed in or on a top surface of the support structure; a second periodic structure having a period, $p_2$, oriented parallel to the first periodic, light diffracting structure and disposed in the support structure at a selected distance below the first periodic, light diffracting structure; and a sensor disposed in the support structure at a selected distance below the first periodic, light diffracting structure and the second periodic structure.

An embodiment of the invention is a lens-less light-field detector that includes a detector support structure; a first pixel device, and a second pixel device disposed linearly adjacent the first pixel device. The first pixel device comprises a first periodic, light diffracting structure having a period, $p_1$, disposed in or on a top surface of the support structure; a second periodic structure having a period, $p_2$, oriented parallel to the first periodic, light diffracting structure and disposed in the support structure at a selected distance below the first periodic, light diffracting structure, wherein the second periodic structure is not laterally displaced from the first periodic, light diffracting structure; and a first sensor disposed in the support structure at a first selected distance below the first periodic, light diffracting structure and the second periodic structure. The second pixel device comprises a first periodic, light diffracting structure having a period, $p_1$, disposed in or on a top surface of the support structure; a second periodic structure having a period, $p_2$, oriented parallel to the first periodic, light diffracting structure and disposed in the support structure at the selected distance below the first periodic, light diffracting structure, wherein the second periodic structure is laterally displaced from the first periodic, light diffracting structure by an amount $(m_2/n_2)p_1$; and a second sensor disposed in the support structure at the first selected distance below the first periodic, light diffracting structure, wherein m, n are positive integers, $\lambda$ is the wavelength of an monochromatic, plane, incident wavefront on the first periodic, light diffracting structure, $p_1$ is greater than $\lambda$. According to an aspect, the first and second pixel devices further comprise a first intermediate periodic, light diffracting structure having a period, $p_1$, disposed between the first periodic, light diffracting structure and the second periodic structure, oriented perpendicularly to the first and second periodic structures; and a second intermediate periodic, light diffracting structure having a period, $p_2$, disposed between the second periodic structure and the first and second sensors, oriented perpendicularly to the first and second periodic structures, wherein in the first pixel device, the first and second intermediate periodic, light diffracting structures are not laterally displaced from the respective first and second periodic structure, further wherein in the second pixel device, the first and second intermediate periodic, light diffracting structures are laterally displaced from the respective first and second periodic structures by an amount $(m_2/n_2)p_1$. According to an aspect, the detector further comprises at least an $n^{th}$ ($n \geq 3$) pixel device disposed linearly adjacent the $(n^{th}-1)$ pixel device, including a first periodic, light diffracting structure having a period, $p_1$, disposed in or on a top surface of the support structure; a second periodic structure having a period, $p_2$, oriented parallel to the first periodic, light diffracting structure and disposed in the support structure at the selected distance below the first periodic, light diffracting structure, wherein the second periodic structure is laterally displaced from the first periodic, light diffracting structure by an amount $(m_n/n_n)p_1$, where $(m_n/n_n) > (m_{n-1}/n_{n-1})$; and an $n^{th}$ sensor disposed in the support structure at the first selected distance below the first periodic, light diffracting structure. In a further aspect, every $n^{th}$ ($n \geq 3$) pixel device further comprises a first intermediate periodic, light diffracting structure having a period, $p_1$, disposed between the first periodic structure and the second periodic structure, oriented perpendicularly to the first and second periodic structures; and a second intermediate periodic, light diffracting structure having a period, $p_2$, disposed between the second periodic structure and the $n^{th}$ sensors, oriented perpendicularly to the first and second periodic structures, wherein in every $n^{th}$ ($n \geq 3$) pixel device, the first and second intermediate periodic, light diffracting structures are laterally displaced from the first periodic structure by an amount $(m_n/n_n)p_1$, where $(m_n/n_n) > (m_{n-1}/n_{n-1})$.

Another embodiment of the invention is a lens-less light field imaging device comprising a two-dimensional, M×N array of ASP-light-field detectors as set forth herein, where M, N are integers equal to or greater than one.

According to all of the foregoing embodiments, the periodic diffracting structures may be of various forms including, but not limited to, diffraction gratings, parallel wire arrays, Ronchi rulings, and others well known in the art. Diffracting apertures may be in the form of slits or other aperture shapes. Gratings may advantageously be made of metal. The sensor may be, without limitation, one of a reverse-bias p-n junction diode, a forward-biased diode, a p-i-n diode, a charge-coupled device (CCD), or a single-photon avalanche diode. A device may incorporate one or more color filters if, for example, the incident light has a broad spectrum that may advantageously be narrowed.

An embodiment of the invention is directed to a method for determining a direction of incident light from an object, comprising creating a periodic, interference pattern of the incident light from the object, detecting the interference pattern and, determining a phase shift of the pattern relative to a reference position based upon the relative illumination of different diodes.

Embodiments of the invention thus pertain to imaging devices and methods that can enable extraction of information relating to the three-dimensional structure of the object light. Each ASP in the type of imager described herein may extract the incident angle of light as well as its brightness. Individual ASPs may be used to localize one or more light sources (such as for sun tracking, for example). When many such ASPs are combined in an array, such information may be used to reconstruct three-dimensional surfaces, or multiple distinct points in 3-D space, which may have application in, e.g., biological imaging. An imaging device according to embodiments of the invention may advantageously be built in a standard semiconductor manufacturing process such as those used to build microprocessors and present day digital camera imagers; for example, standard CMOS fabrication processes.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention, and together with the description serve to explain the principles and operation of the invention.

BRIEF DESCRIPTION OF THE DRAWINGS

FIGS. 4a, b diagrammatically show structures for extracting information about diffraction pattern phase according to alternative, exemplary aspects of the invention;

DETAILED DESCRIPTION OF EMBODIMENTS OF THE INVENTION

Figure 1:
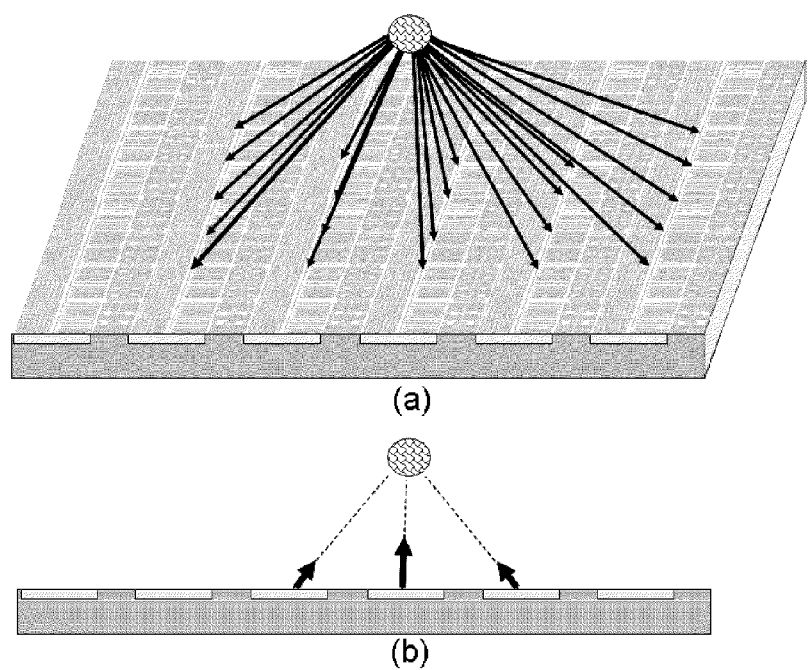
FIG. 1a shows a perspective illustration of a light-field imager and how light from a source strikes each pixel of an array with a distinct incident angle.
FIG. 1b illustrates that if each pixel in an array can determine the incident angle as well as the intensity of the light it detects, then array is able to localize a light source in three dimensions, according to an illustrative embodiment of the invention.

Reference will now be made in detail to the present exemplary embodiments of the invention, examples of which are illustrated in the accompanying drawings.

Embodiments of the invention are directed to angle-sensitive pixel devices and light field image detectors incorporating these ASP devices to measure both the intensity and the incident angle of incident light, and associated methods. The disclosed apparatus and methods utilize the Talbot effect.

The Talbot effect, or the self-imaging property of periodic objects such as diffraction gratings, was first discovered by Henry Fox Talbot in 1836. When an infinite diffraction grating is illuminated by a plane wave normal to its surface, identical images of the grating are formed at certain equally spaced distances behind the grating. FIG. 2a diagrammatically illustrates the parameters of a diffraction grating 102 with incident light 100 (nominally 500 nm wavelength) striking the grating at normal incidence and at a $\theta=5$ degree incident angle. The Talbot effect is a consequence of Fresnel diffraction, and the interference image (diffraction pattern) 104, indicated at arrow 1 as shown in FIG. 2b, forms at integer multiples of the Talbot distance $z_T=2d^2/\lambda$, where d is the period of the grating and $\lambda$ is the wavelength of incident light. Additional, more complex sub-images 105, 106 can be observed at the fractional Talbot distances $z=(m/n)z_T$ (indicated at arrows ½, 3/2), where m and n are positive integers.

A property of the Talbot effect is its response to off-axis illumination. For macroscopic ($d \gg \lambda$) linear gratings illuminated by an off-axis plane wave incident at angle $\theta$, self-imaging is observed at multiples of the distance $z=2\cos^3(\theta)d^2/\lambda$. Furthermore, the images exhibit a lateral shift $\Delta x=z\tan(\theta)$ perpendicular to the grating lines as a result of the off-axis wave propagation.

Multiple sources of off-axis illumination each generate their own set of laterally shifted grating self-images, and these self-images superpose. For small angles, these self-images all form at approximately the same distances, and the superimposed image contains information about the magnitude of illumination as well as direction. The incident angles of light rays striking the grating can be determined by measuring the shift in Talbot self-images.

FIG. 2c graphically shows the light intensity of the Talbot images at a diode plane for normally incident light and light incident at $\theta=5$ degrees. The lateral shift of the diffraction patterns changes with incident angle.

Modern semiconductor manufacturing of standard CMOS circuits allows for the construction of very fine features, on the order of a single wavelength of light, and so allows for the construction of metal diffraction gratings and photodiode arrays that are smaller than the wavelength of visible light. To generate the Talbot effect in a standard CMOS layer stack, the self-images need to form within microns of the diffraction grating. This may require the diffraction grating to have a period of only a few wavelengths. Conventional analyses of diffraction are invalid at these dimensions; however, numerical simulations such as those used to generate FIG. 2, confirm that, even for these geometries, diffraction generates Talbot-like self-images at regular distances. These periodic intensity patterns retain incident angle sensitivity.

The challenge, then, is to extract shifts in these periodic intensity patterns using structures on a pixel scale. For macroscale applications, the simplest approach to measuring these shifts is to place a small array of CCD or CMOS photosensors at the plane of self-image formation. The array captures the self-image directly, which can be used to determine the angle and intensity of incident light. At the microscale, however, the penetration depth of light in silicon limits the resolution of photodiodes to about 1 μm, making it difficult to resolve sub-micron features of the self-image.

A micron-scale light-field imager device requires both a Talbot self-image generator and a structure that can analyzing these images. In order to achieve spatial resolution comparable with existing image sensors, the entire device structure must fit within an area that is at most tens of microns on a side. To produce a reasonably periodic self-image, the grating must have several periods within this area. Together these two constraints suggest using a grating with a period of only a few wavelengths. Contemporary planar photolithography techniques can easily achieve the resolution required to generate appropriate diffraction gratings. Numerical modeling and simulation can accurately predict behavior for finite gratings built on a single-micron scale.

Numerical treatments show that as long as the period is greater than the wavelength of incident light, Talbot-like self-images can be observed in close proximity to a diffraction grating. We have performed simulations using the finite-difference time domain (FDTD) technique and observed patterns as shown in FIGS. 2b and 2c. In particular, starting from the ½ Talbot distance, we observe strong intensity patterns with periodicity identical to the diffraction grating. Additional simulations show that under off-axis illumination, the intensity patterns generated by the high-density gratings shift laterally. An effect of moving to wavelength-scale diffraction gratings is to suppress higher-order fractional Talbot images.

To extract incident angle information about the Talbot pattern, it is necessary to characterize the horizontal offset of the self-images. Previously reported work used gratings (and self images) that were significantly larger (pitch of d=250 μm) than the pixels of the image sensor itself. Thus the image sensor array could directly capture the self-image as a set of electrical signals. However, in a micron-size device according to an aspect of the invention, the high density imager array would require a pixel pitch of ¼ the grating pitch (e.g., on the order of 200 nm) to effectively resolve the features of the Talbot image. Although sub-micron photosensors can be built, the images they capture tend to be blurred by diffusion effects, limiting their actual resolution to 1 μm or worse.

A solution provided by an embodiment of the invention includes a second parallel analyzer grating 304 of identical period to the first grating 302 disposed at the self-image plane, as illustrated in FIGS. 3a, 3b. The second (analyzer) grating 304 uses the Moire effect to filter the Talbot image. When the intensity peaks align with gaps in the second grating as shown in FIG. 3b, light passes through the analyzer grating 304. When the intensity peaks are out of alignment (FIG. 3a), the bars of the analyzer grating block the light. By placing a single large photosensor under the analyzer grating and measuring the total light flux, we can extract the alignment of the self-image with the analyzer grating (FIG. 3c).

FIG. 4b shows an exemplary, diagrammatic illustration of such a structure embodiment 300-2 for extracting partial information about the diffraction pattern phase. Two metal gratings 302a, 302b are placed at a 90 degree lateral offset relative each other over a single, large well-diode 307 integrated into substrate 310. Separate pixels with gratings shifted by 0, 180 and 270 degrees or, alternatively, 0, 120 and 240 degrees, for example, would extract full angle information. This approach decouples the design of the diodes from that of the gratings, allowing for better diodes. Also, because the finest features in this aspect are the gratings themselves rather than the photodiodes, the same class of structure can be built using lower resolution photolithography (i.e., in a larger feature size, cheaper manufacturing process).

Figure 5:
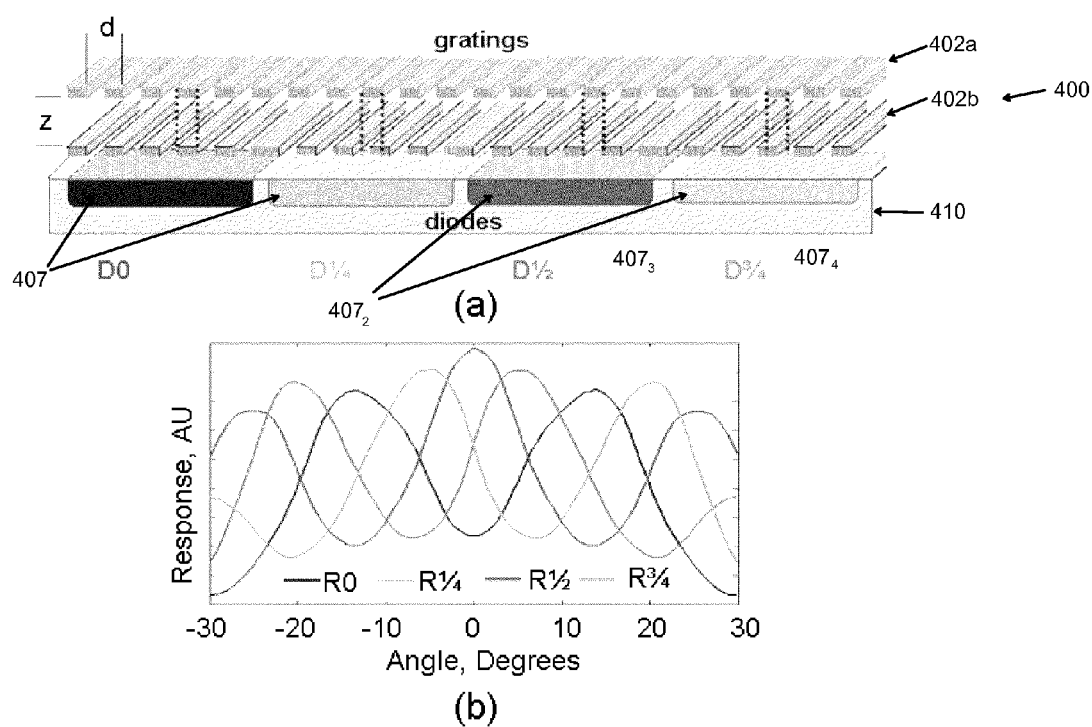
FIG. 5a illustrates an ASP device having multiple, adjacent, single deep-well photodiodes and stacked, offset gratings disposed above (black dotted lines illustrate relative alignment of the gratings.
FIG. 5b shows simulation results for various offsets: note that the incident angles that generate peak responses shift proportionally with the offset of the grating, according to an embodiment of the invention.

The total light flux detected is dependent on both the overall source brightness and the incident angle. This may lead to an ambiguity between intensity and angle in the sensor output, since a bright source at a blocked angle yields the same sensor output as a dimmer source at an angle passed by the analyzer grating. To disambiguate angle and intensity, in accordance with an aspect of the invention as illustrated in FIG. 5a, a detector 400-2 includes n (n=4 as shown) single well-diode sensors 407 integrated in substrate 410, and two stacked gratings 402a, 402b disposed above in close proximity so that they see approximately the same light field. Each diode has a different relative offset between the analyzer grating 402b and the image-generating grating 402a. Using the unique signals produced by each of the set of sensors, one can recover intensity and incident angle.

Simulated responses for one set of four sensors under plane illumination of different angles are shown in FIG. 5b. It is seen that the transmission through the analyzer grating is periodic in incident angle due to the lateral shift of the periodic self-images. The responses of these sensors can be approximately modeled by the equations:

$$R_0 = I_0(1 - m\cos(b\theta))F(\theta)$$

$$R_{1/4} = I_0(1 + m\sin(b\theta))F(\theta)$$

$$R_{1/2} = I_0(1 + m\cos(b\theta))F(\theta)$$

$$R_{3/4} = I_0(1 - m\sin(b\theta))F(\theta) \quad (1)$$

where $I_0$ is proportional to incident intensity, $\theta$ is incident angle, m is a measure of the modulation depth, and b is a measure of angular sensitivity. $F(\theta)$ is an even-symmetric function included to account for surface reflections and other effects that reduce responses to high angle incident light independent of angular sensitivity.

From the four outputs in equation 1, it is possible to determine the intensity and incident angle (in the x-z plane) of light. Summing the ASP responses $R_0$ and $R_{1/2}$ (or $R_{1/4}$ and $R_{3/4}$) removes the modulation produced by incident angle and provides information on overall intensity.

$$I_0 F(\theta) = \frac{R_0 + R_{\frac{1}{2}}}{2} = \frac{R_{\frac{1}{4}} + R_{\frac{3}{4}}}{2} \quad (2)$$

Incident angle can be extracted as:

$$\theta = \frac{1}{b}\tan^{-1}\frac{R_{\frac{1}{4}} - R_{\frac{3}{4}}}{R_{\frac{1}{2}} - R_0} \quad (3)$$

Figure 6:
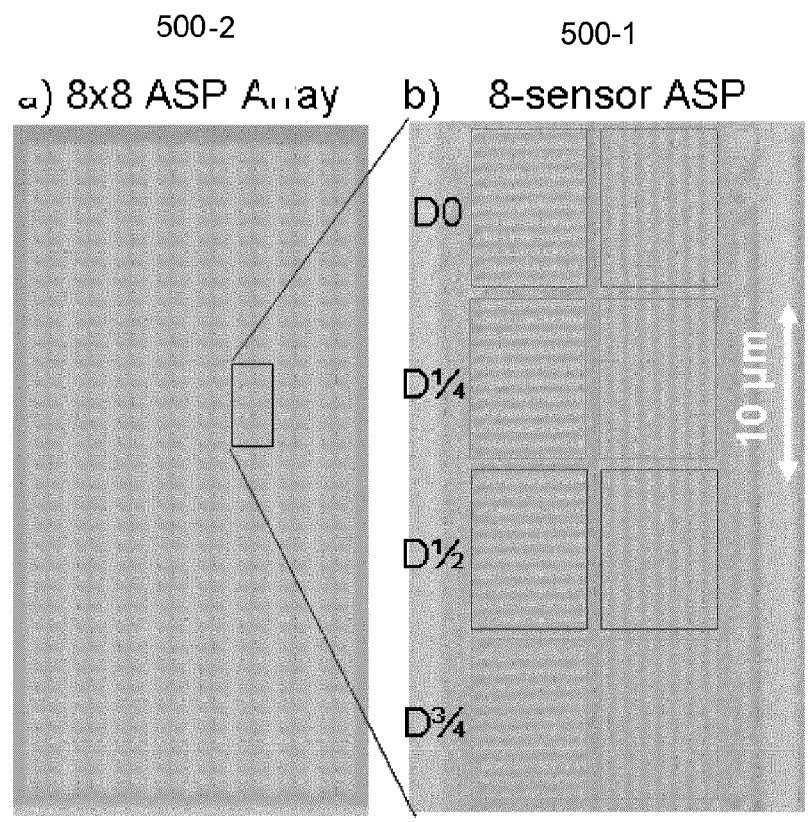
FIGS. 6a, b are microphotographs of a) one ASP, and b) an 8×8 array of ASPs, manufactured in 130 nm CMOS, according to an embodiment of the invention.

Because the lateral shift of the Talbot images is observed only for off-axis illumination at angles perpendicular to the grating lines, the device 400-2 is responsive only to angles in one direction. In order to obtain full illumination angle information, a second set of identical devices with gratings rotated by 90 degrees, in close proximity to the first, were provided. This second set is responsible for measuring the angle information ignored by the first set of sensors. A complete angle-sensitive pixel (ASP) 500-1 composed of eight different sensors placed in close proximity is shown in FIG. 6b. Four sensors are responsible for the angle in the x-z plane; four more are needed for the angle in the y-z plane. For both x-z and y-z gratings, diffraction-analyzer offsets of 0, d/4, d/2 and 3d/4 were used. The analyzer gratings were positioned at the ½ Talbot distance, the smallest distance where self-images with periodicity identical to the diffraction grating are found. An 8×8 ASP array light field image sensor 500-2 manufactured in a digital 130 nm CMOS fabrication process is illustrated in the photomicrograph of FIG. 6a.

The overall size of the exemplary eight-sensor ASP 500-1 is 20 μm by 40 μm, with each individual sensor being 10μm square. The stacked diffraction gratings were built in wiring layers, above intrinsic p-n junction photodiodes. In this illustrative example, each grating in each of the eight sensors was a Ronchi ruling (equal width bars and gaps) using copper bars with a period of 880 nm All other space was filled with silicon dioxide. One set of gratings was used to bus out the data generated, which eliminated the need for wiring lanes in the array. As the gratings provide a large number of bus lines, the eight ASP outputs are read in parallel. The grating separation, z, was limited by available interconnect layer spacing, and pitch d chosen from numerical simulations to maximize modulation depth, m, for green (525 nm in vacuum, 350 nm in oxide) light. For the device 400-1 shown in FIG. 5a, empirical simulations for green ($\lambda$=525 nm in vacuum) light determined the ½ Talbot distance in silicon dioxide to be 2 μm. The top diffraction grating was positioned in the 6th metal layer and the analyzer grating in the 3rd metal layer, for a separation of 2 microns. A single p-n photodiode in each of the eight sensors measured the total light flux through the stacked gratings. A standard 3T active pixel sensor was used to buffer the photodiode outputs, and several multiplexers allowed access to each ASP individually.

Figure 7:
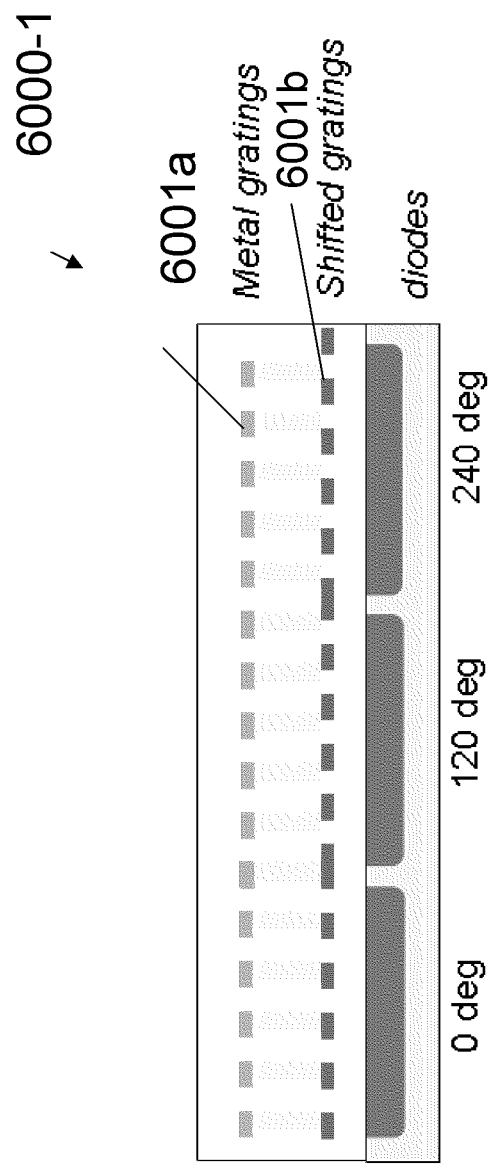
FIG. 7 is a diagrammatic cross sectional view of an image sensor according to an alternative aspect of the invention.

FIG. 7 shows an illustrative aspect of a device embodiment 6000-1 similar to that shown in FIG. 5a in which three single diodes 6007, 6008, 6009 are disposed adjacent two grating layers 6001a, 6001b. Second grating layer 6001b is shifted relative to grating 6001a by 0, ⅓ and ⅔ of the grating period.

Figure 8:
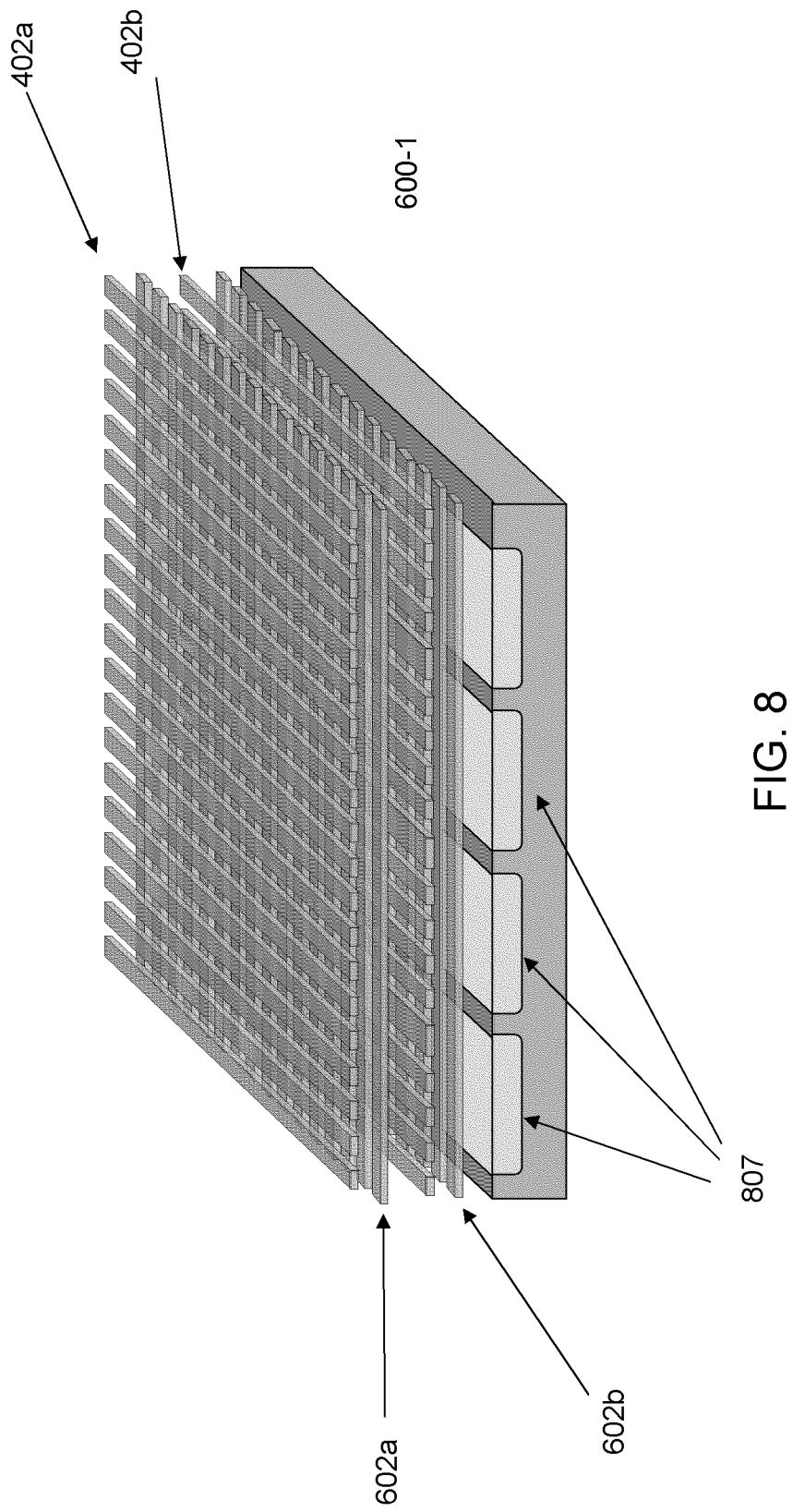
FIG. 8 is a perspective view of an ASP-based light field image device according to an embodiment of the invention.

According to an alternative aspect, a light field image detector 600-1 is illustrated in FIG. 8. In this aspect, a second set of gratings 502a, 502b rotated by 90 degrees and interleaved between grating 402a, 402b are provided in close proximity thereto. This second set of gratings is responsible for measuring the angle information ignored by the first set of sensors.

To test our ASP, a light source (commercial green LED, with center wavelength of 525 nm and spectral width of 32 nm) was mounted on a variable angle arm at a fixed distance from the fabricated arrays. No additional collimation or filtering was performed, as a non-ideal illumination source better approximates real-world imaging applications. When a range of wavelengths are present, the self-images observed are a superposition of the intensity patterns produced by each wavelength. The spectral width of the source is relatively narrow and the path length differences, which make the Talbot patterns, are shorter than the source's coherence length, so we did not expect significant deviation in performance from our monochromatic, coherent simulations.

Figure 2:
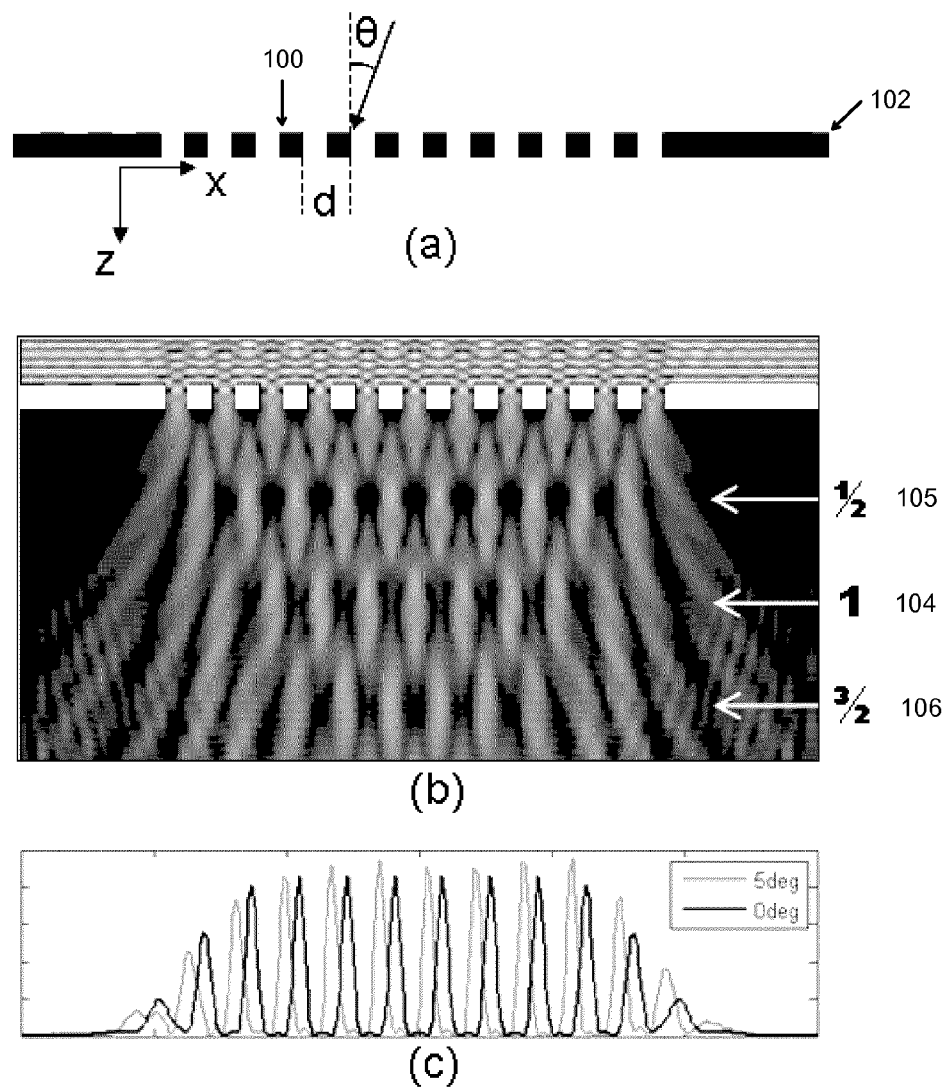
FIG. 2a is a cross sectional, schematic view of a diffraction grating with a definition of scale and dimensions.
FIG. 2b shows FDTD simulations of the Talbot effect for light normally incident on the grating, and the self images at multiples of the ½ Talbot depth.
FIG. 2c is a plot based on an FDTD simulation showing the lateral shift of the self image at the ½ Talbot depth with shifting incident angle from θ=0° to 5°, according to an illustrative embodiment of the invention.
Figure 3:
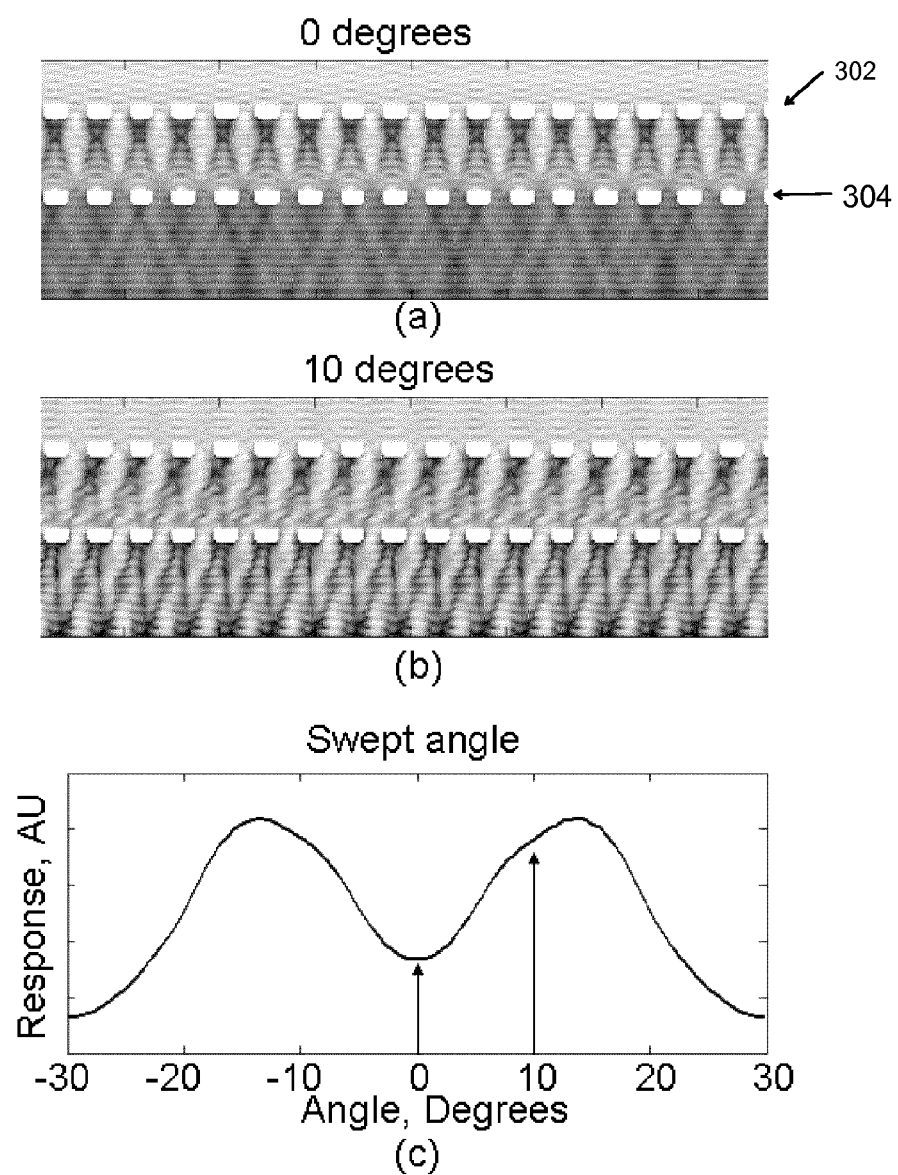
FIG. 3: FDTD simulations illustrating the effect of including an analyzer grating at the ½ Talbot depth: a) When the peaks of the self-image align with the bars of the analyzer grating, little light passes through to a light detector below; b) When the incident angle is shifted so that the peaks align with gaps in the analyzer grating, much more light passes to the detector; c) Intensity of detected light changes periodically with swept incident angle, according to an illustrative embodiment of the invention.
Figure 9:
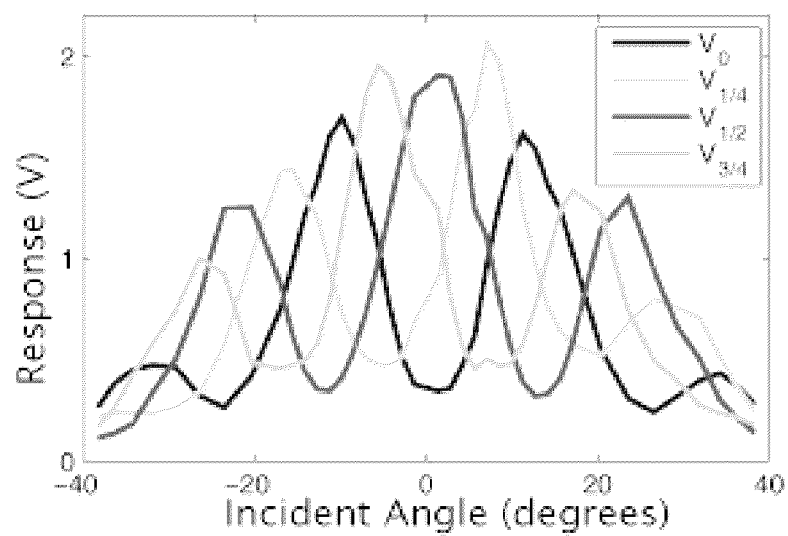
FIG. 9 is a graph showing measured responses of an ASP as incident angle is swept, according to an illustrative aspect of the invention.

We recorded the outputs of a single ASP for each angle as the source was moved. The outputs corresponding to one set of four sensors in the ASP are shown in FIG. 9. Reasonable agreement was obtained between measured results and those predicted by simulation. Fitting the curves in FIG. 9 with the model in equation (1) gives b=15 and m=0.7, with a root-mean-squared error of 9%. The second set of four sensors (for characterizing angles in the y-z plane) produced similar curves in response to changes in incident angle. Differences observed between measurement and idealized simulations such as those in FIGS. 2 and 3 are due to reflection off the silicon dioxide surface, manufacturing variation, and the finite gratings actually used. However, our simulations reasonably characterized the angular sensitivity and modulation depth of the ASP.

Fine-pitch gratings are known to polarize the light they transmit. A recent study on the polarization-dependent Talbot effect in high-density gratings predicts that gratings with period of approximately 2.5 $\lambda$, should show significant polarization sensitivity. Specifically, the Talbot self-images formed at the ½ Talbot distance by TE (electric field parallel to the grating lines) polarized light should be approximately twice as bright as those formed by TM (magnetic field parallel to the grating lines) polarized light. Our observations are in good agreement with this prediction: when we rotated the polarization of the incident light on our ASP from TE to TM, the overall observed intensity decreased by a factor of 2.05. However, both angular sensitivity b and modulation depth m changed by less than 10%. These characteristics indicate that the TM-polarized Talbot self-images are weaker than the TE-polarized self-images, but otherwise behave similarly in their encoding of angle and intensity information.

Figure 10:
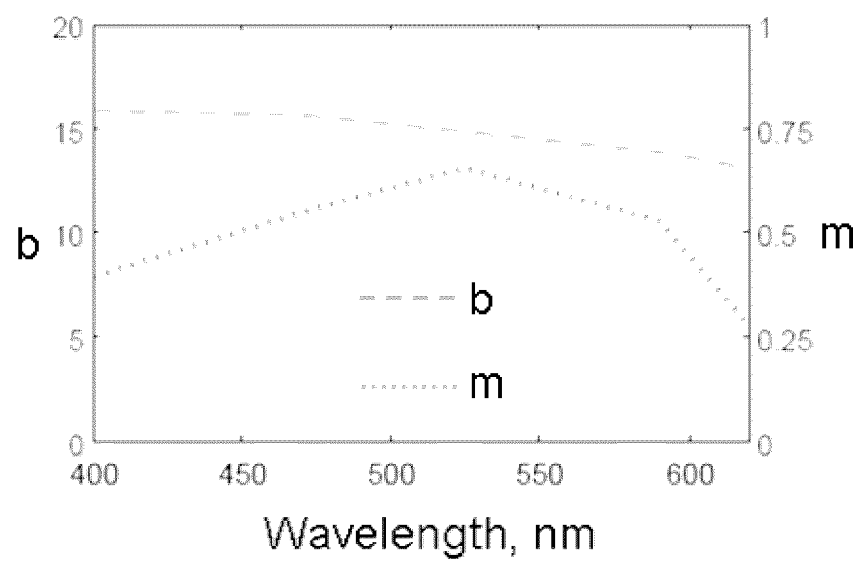
FIG. 10 is a graph showing the measured effect of wavelength on angular sensitivity, b, and modulation depth, m, according to an illustrative aspect of the invention.

The design was optimized for $\lambda$=525 nm, but we tested it across a range of wavelengths from 400 nm to 620 nm We expected little change in angle sensitivity b in response to changes in wavelength, as the Talbot self-images do not change in periodicity with changes in $\lambda$. This prediction was born out by measurement, as can be seen in FIG. 10: b was only weakly sensitive to $\lambda$ over the range 400 nm to 620 nm However, changes in wavelength significantly change the Talbot distances. The analyzer grating was not optimally positioned when $\lambda \neq 525$ nm, so the observed self-images were blurred, and modulation depth, m, degraded. Over this range of wavelengths, we recover angle information less efficiently, but the angle sensitive function does not vanish. The fact that the ASP works across such a range of wavelengths is a direct consequence of analyzing the self-image at the ½ Talbot distance, where the relative depth of the Talbot pattern is least sensitive to $\lambda$.

Figure 11:
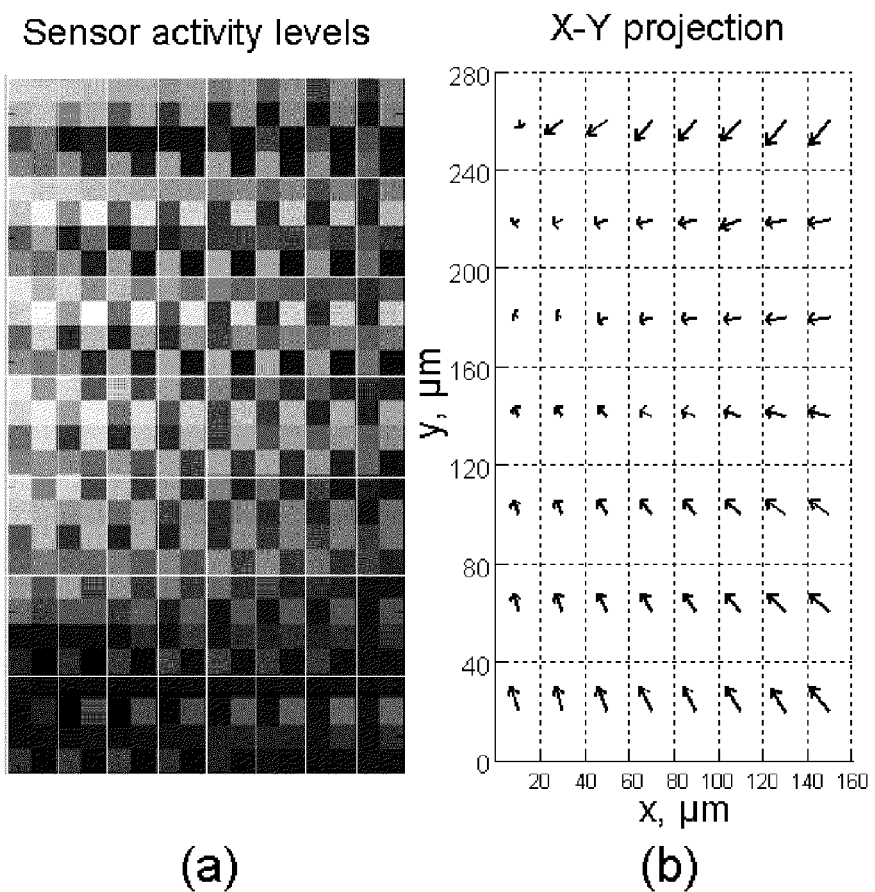
FIG. 11 shows the measured ASP array response to a light source held 500 µm above the array and slightly to the left: a) Responses of individual sensors, where brighter squares represent more heavily illuminated sensors and white lines delimit individual ASPs; b) Computed incident angle for each ASP (projected into the x-y plane), according to an illustrative aspect of the invention.

To confirm the light-field imaging capability of our sensors, we placed a multimode fiber tip 500 µm directly above the ASP array. After coupling light from a light emitting diode (identical to the one used in single ASP tests) into the fiber, light exiting the fiber will have a conical profile, and thus a simple divergent light field at the plane of the array. We recorded from all 64 sites on the ASP array and measured the output of each sensor, as shown in FIG. 11a. As can be seen, adjacent sensors tuned to different angles responded very differently, and their relative responses depend upon their overall location relative to the light source. Applying equation (3) and the angle response data shown in FIG. 9, we reconstructed the light vectors for each ASP, as shown in FIG. 11b.

Figure 12:
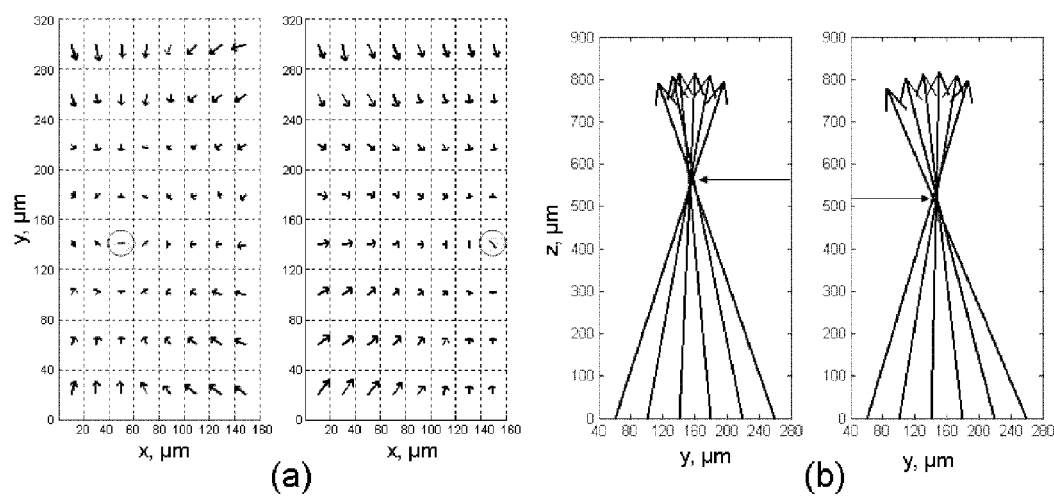
FIG. 12 shows how an 8×8 ASP array accurately resolves light source locations in 3-D space: a) The measured light-vector field due to a source 550 µm above the array can clearly reconstruct lateral shifts in location (in this case by 100 µm); b) The measured light-vector field can also be used to reconstruct changes in depth (z) of a light source, in this case by 50 µm, according to an illustrative aspect of the invention.

To further confirm the capabilities of our array, we moved the light source to various locations in three-dimensional space above the array. At each position we recorded the sensors' responses and reconstructed the incident angle of light coming from the fiber. The array could be used to accurately reconstruct the location of the light source in two dimensions, as shown in FIG. 12a, where the source was moved by 100 µm in the x-direction, and the computed incident angles reflect this. More strikingly, the array could be used to accurately localize the light source in the third, z direction, accurately capturing a 50 µm shift in the height of the source above the array, as shown in FIG. 129b. Thus an array of ASPs is able to accurately reconstruct the three-dimensional structure of simple light sources, providing information beyond what is available from the intensity map available from a standard image sensor.

FIG. 4a shows a cross sectional schematic of a non-limiting exemplary device embodiment 300-1 of the invention. The device includes a metal slit grating 301 and a substrate 310 with multiple linear arrays of two integrated, interleaved fingered diodes (A) 307, (B) 308 that are relatively shifted by 180 degrees (i.e., offset by zero and one-half period of the grating) relative to the grating. Multi-finger diodes advantageously provide maximum photon capture.

Figure 13:
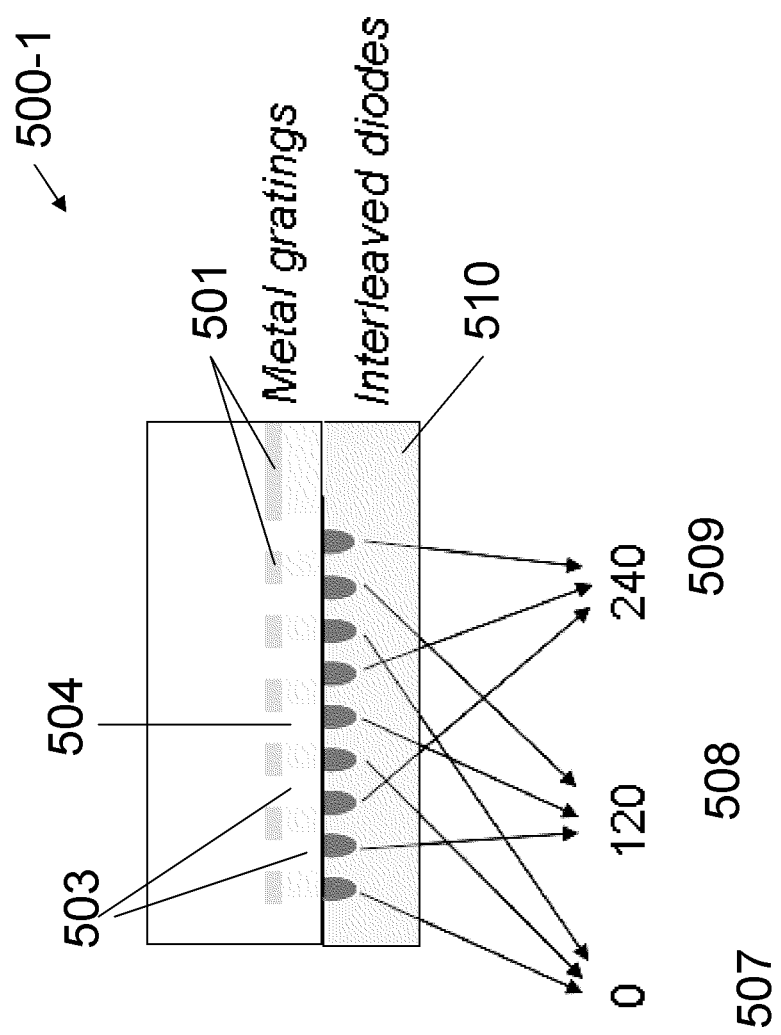
FIG. 13 is a diagrammatic cross sectional view of an image sensor according to an alternative aspect of the invention.

FIG. 13 shows an imaging device 500-1 based upon a three-diode structure according to a non-limiting exemplary embodiment of the invention. The device includes a metal transmission grating 501 having multiple, periodic slit apertures 503. The light shadings indicated by reference numeral 504 do not represent any physical part of the device, rather merely the alignment between the grating and the diodes. The device further includes a single structure of three linear arrays of three interleaved diodes, 507, 508, 509, integrated in a substrate 510. The three illustrated diodes of diode array 507 are aligned with the grating (no offset) and thus will detect a zero degree phase shift in the interference pattern (not shown). Similarly, the three illustrated diodes of diode array 508 are offset by ⅓ of the grating period and thus detect a 120 degree phase shift; while the three illustrated diodes of diode array 509 are offset by ⅔ of the grating period and thus detect a 240 degree phase shift.

Figure 14:
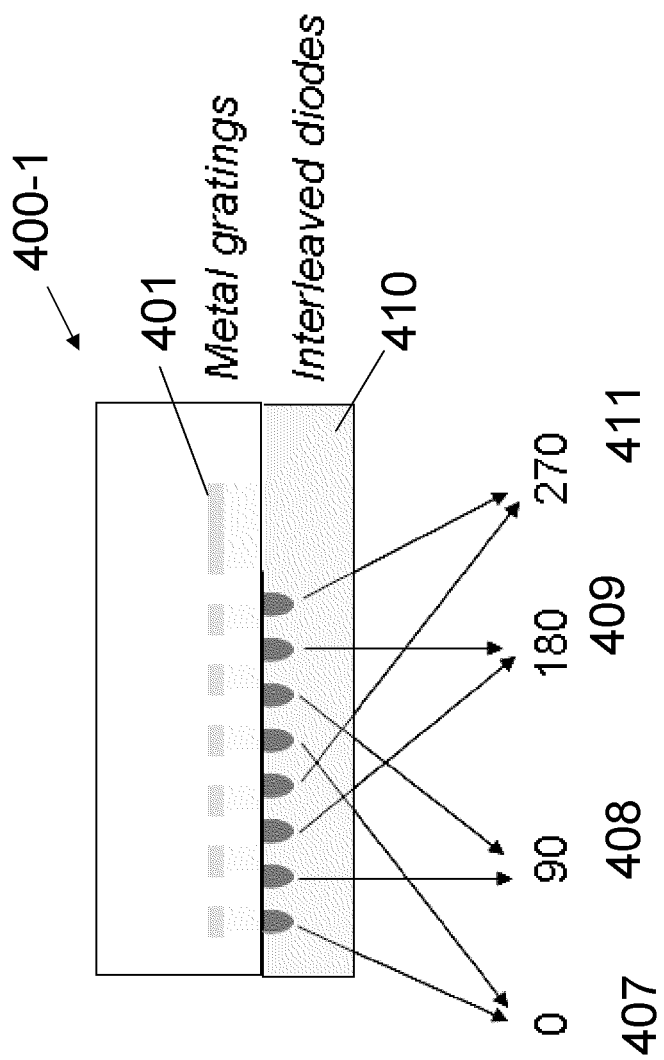
FIG. 14 is a diagrammatic cross sectional view of an image sensor according to an alternative aspect of the invention.

FIG. 14 shows an alternate device arrangement 400-1 of diodes and grating according to a non-limiting, exemplary embodiment. As shown in FIG. 14, an integrated, single-interleaved set of four diodes 407, 408, 409, 411 are positioned offset by zero, ¼, ½ and ¾ of the grating 401 period providing respective phase shifts of 0°, 90°, 180° and 270°. Note that the single-interleaved set of four diodes is different than, e.g., the two adjacent diode sets as shown in FIG. 4a. Again, the light shadow areas in the figure do not reflect any additional physical structure; rather, they only indicate alignment between diodes and metal.

Figure 15:
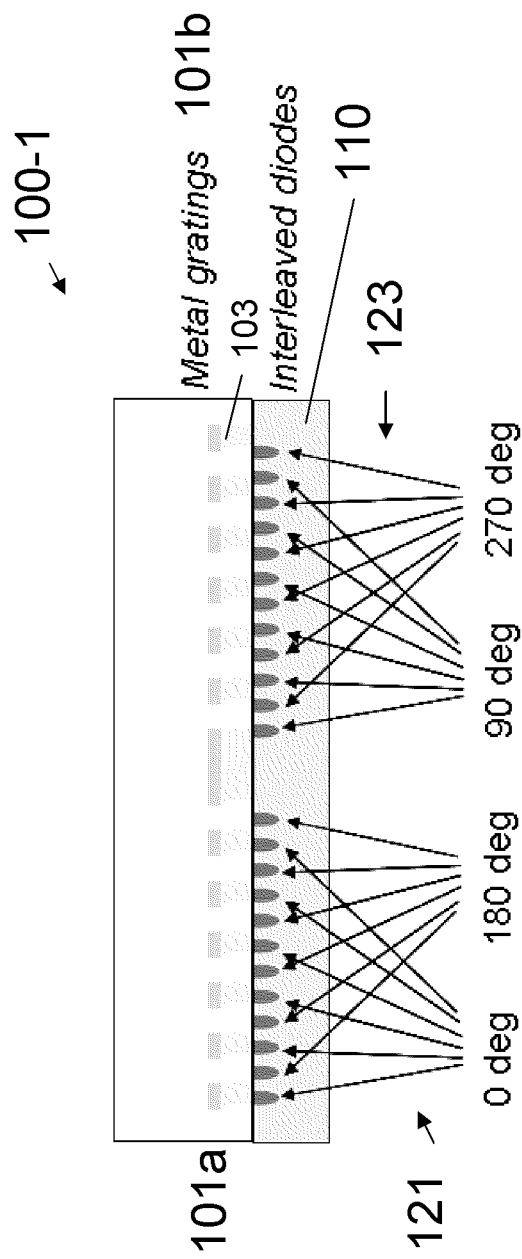
FIG. 15 is a diagrammatic cross sectional view of an image sensor according to an alternative aspect of the invention.

FIG. 15 shows a cross-sectional schematic of a detector device 100-1 according to an alternative, non-limiting exemplary embodiment of the invention. Sensor device 100-1 incorporates one set of interleaved diodes 121 at 0 and 180 degrees relative to the grating and another set of interleaved diodes 123 at 90 and 270 degrees. This type of arrangement may prevent diode overlap. The two shifted gratings 101a, 101b are shown as darkly shaded while the lighter shading 103 beneath each grating is presented merely to show the alignment between the grating and the diodes and does not represent any physical structure of the device.

Figure 16:
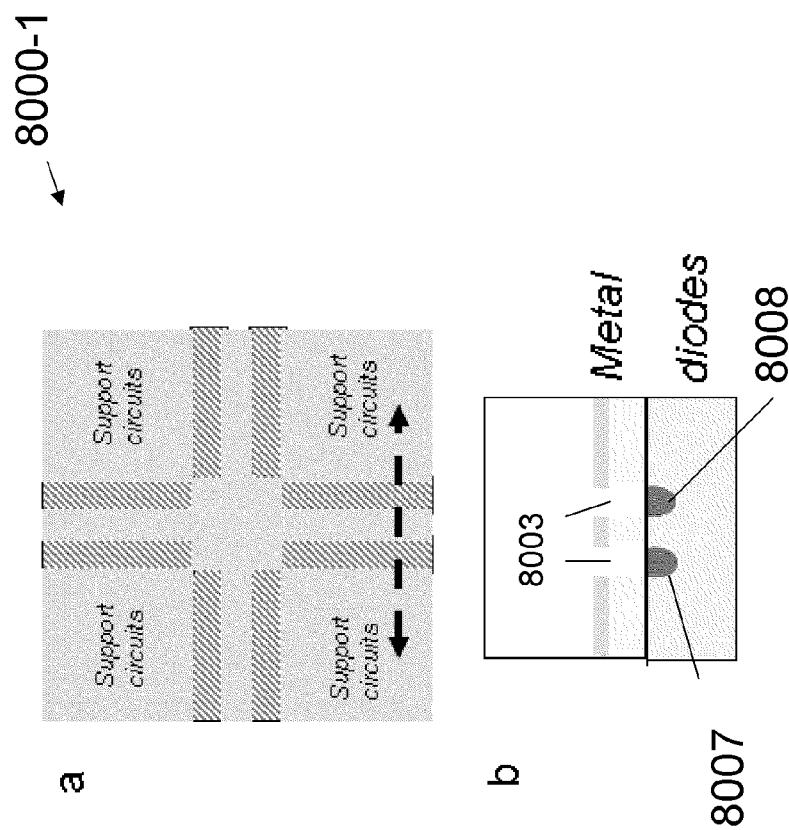
FIGS. 16a, 16b are, respectively, a top view and a cross sectional of an alternate imaging sensor according to an illustrative aspect of the invention.

FIG. 16a shows a top view of components of a non-limiting, exemplary device aspect 8000-1 incorporating just two slits 8003 and two diodes 8007, 8008. FIG. 16b is a cross-sectional view through the dashed line in FIG. 12a. This design is compact, allowing for higher spatial resolution.

Figure 17:
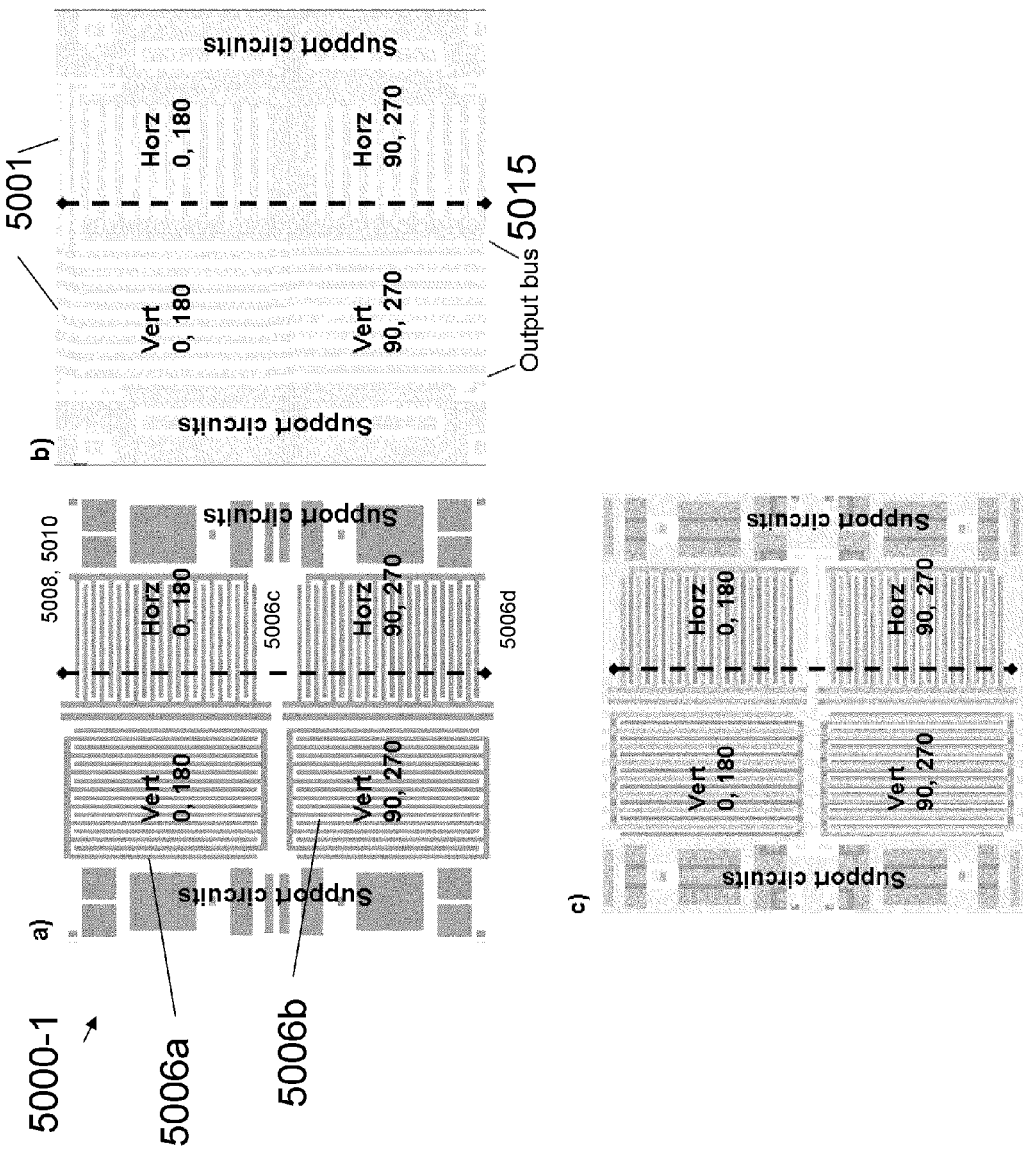
FIGS. 17(a-c) show top cross sectional plan views of a full interleaved diode light-field sensor cell according to an exemplary embodiment of the invention.

FIGS. 17(a-c) show top views of components of a non-limiting, exemplary full interleaved diode light-field sensor cell 5000-1, having gratings and diodes in both the vertical (5006a, b) and horizontal (5006c, d) orientations, which may be used to capture both azimuth and altitude information about the source object. FIG. 17a illustrates the layout of diodes (e.g., n-type diffusion in p-substrate), wherein each set of vertically-oriented diodes 5006*a, b* contains a pair 5002, 5004 of interleaved diode arrays and each set of horizontally-oriented diodes 5006*c, d* contains a pair 5008, 5010 of interleaved diode arrays. FIG. 17*b* shows the associated metal gratings 5001 with the same orientations as the corresponding diode arrays. As further shown in FIG. 17*b*, the vertically-oriented gratings may be used as a data bus to carry information from each column to the edge of the array at 5015 without giving up area in the imager itself. Alternatively, the gratings may be used to tie many individual diodes to processing circuits away from the array itself. This maximizes the photosensitive area of the imager, recovering area lost to circuits required to convert light into electrical signals. FIG. 17*c* shows an overlay of diodes and gratings shown in FIGS. 17*a, b*. FIG. 15, which shows a cross-section of the horizontally-oriented detectors (i.e., along the dashed black line in FIGS. 17*a-c*), illustrates that the relative alignment of the diodes and metal grating are shifted for the 0/180° cases versus the 90/270° case.

Figure 18:
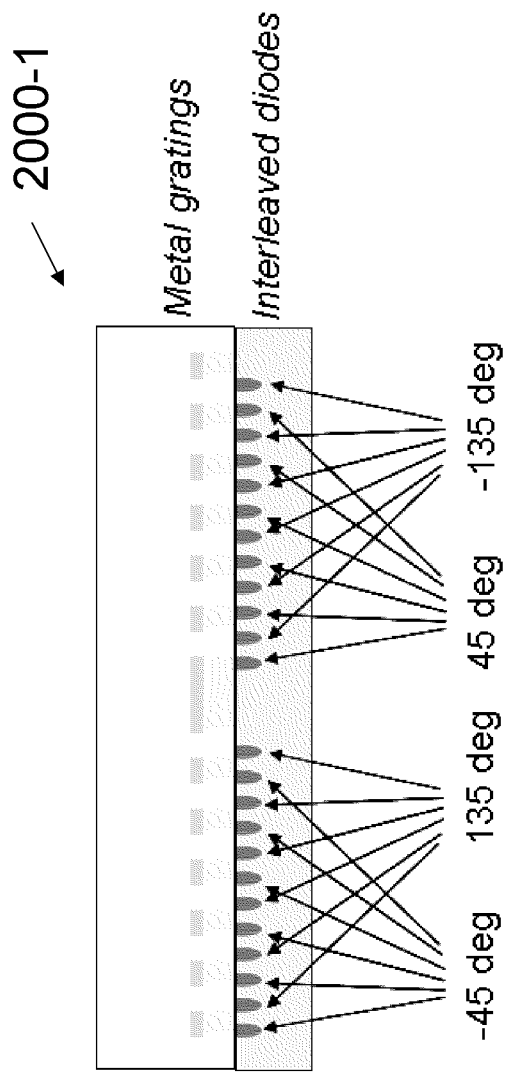
FIG. 18 is a diagrammatic cross sectional view in which all of the diodes are shifted by ⅛ of the metal grating pitch, according to an illustrative aspect of the invention.

FIG. 18 shows an exemplary device aspect 2000-1 similar to that of 100-1 except that all diodes are shifted by ⅛ of the grating pitch, representing phase shifts of −45°, 135°, 45° and −135°. This figure illustrates that the precise alignment of diodes and metal is less important than the relative alignment of diodes to each other. The ⅛ period shift should have no appreciable effect on the function of the structures disclosed herein. This insensitivity applies to all structures disclosed herein, and to the alignment of secondary gratings in the "double grating" embodiments described herein.

Figure 19:
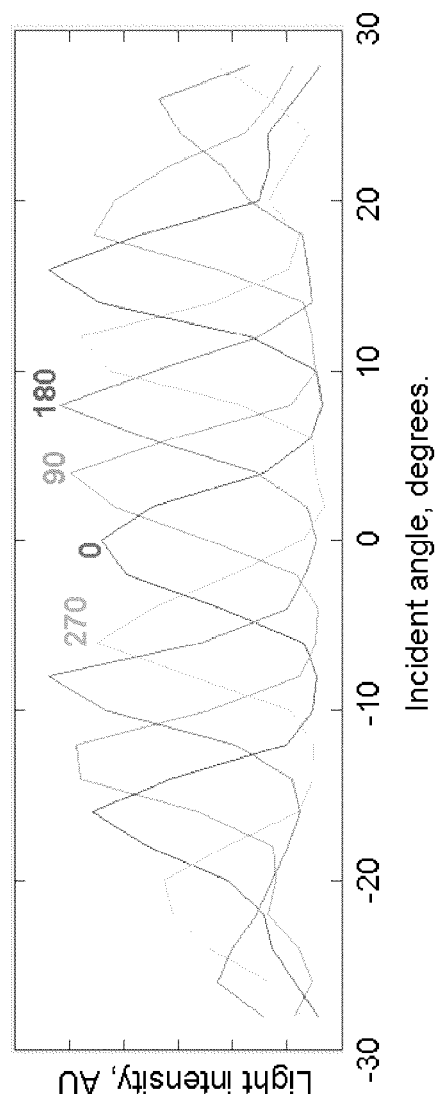
FIG. 19 graphically shows simulated photocurrents from four distinct diode arrays at 0, 90 180 and 270 degrees relative to a grating where the incident angle was swept from −30 to 30 degrees, according to an illustrative aspect of the invention.

FIG. 19 graphically shows simulated photocurrents from four distinct diode arrays at 0, 90 180 and 270 degrees relative to a grating where the incident angle was swept from −30 to 30 degrees, according to an illustrative aspect of the invention. As can also be seen from FIG. 19, each diode shows multiple peaks, indicating that equations (1) may not necessarily lead to a unique angle extraction. This may be remedied by using multiple structures with different grating geometries (and therefore different values of "k"), placed adjacent to each other. If the mapping from incident angle to diode response is different, then different peaks of activity may be distinguished. This may then facilitate construction of a sensor that is able to cover the entire range of incident angles.

In the ideal case where each diode is responding to exactly the same incident angle of light, one may expect some redundancy in the responses in the eight diode aspect described above. For example, $$D0+D180=D90+D270,$$

implying that maintaining all four separate signals may be redundant. This redundant information may be removed by redefining the response in terms of three numbers:
D0−D180,
D90−D270, and
D0+D180+D90+D270.
This recoding could be performed in either the analog or digital domain on the same integrated circuit as the sensors and gratings.

Figure 20:
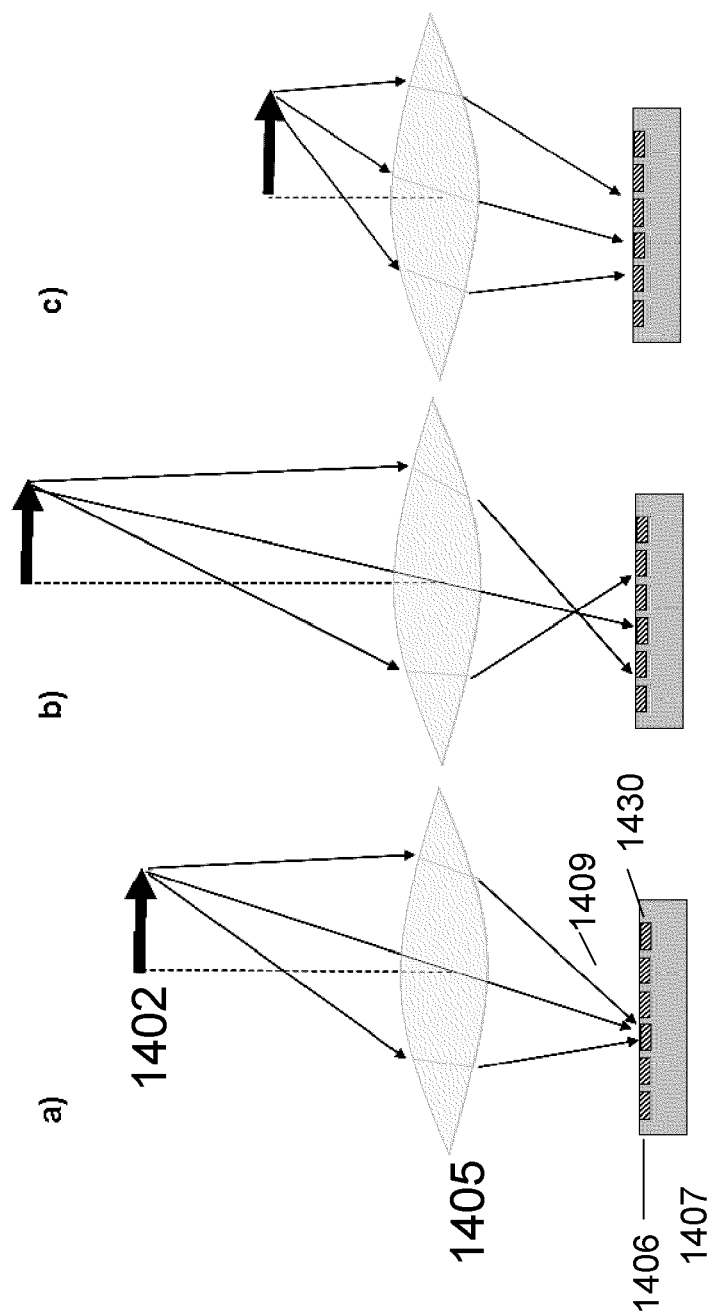
FIGS. 20(a-c) schematically illustrate the use of incident angle data to compute 3-D locations in conjunction with a lens system, according to an exemplary embodiment of the invention.

If incident angle is not constant across the imager (as would be the case in FIGS. 1*b* and 20(*a-c*)), then adjacent gratings will not see identical incident angles. Since the four diodes, D0, D90, D180 and D270 are not all interleaved with each other, but appear in adjacent pixels, they may encode slightly different incident angles, and so contain some non-redundant information that would be lost in recoding. Nonetheless, recoding signals can provide benefits by allowing for different weighting of different components of the data before conversion to digital signals or before transmission off chip.

Figure 21:
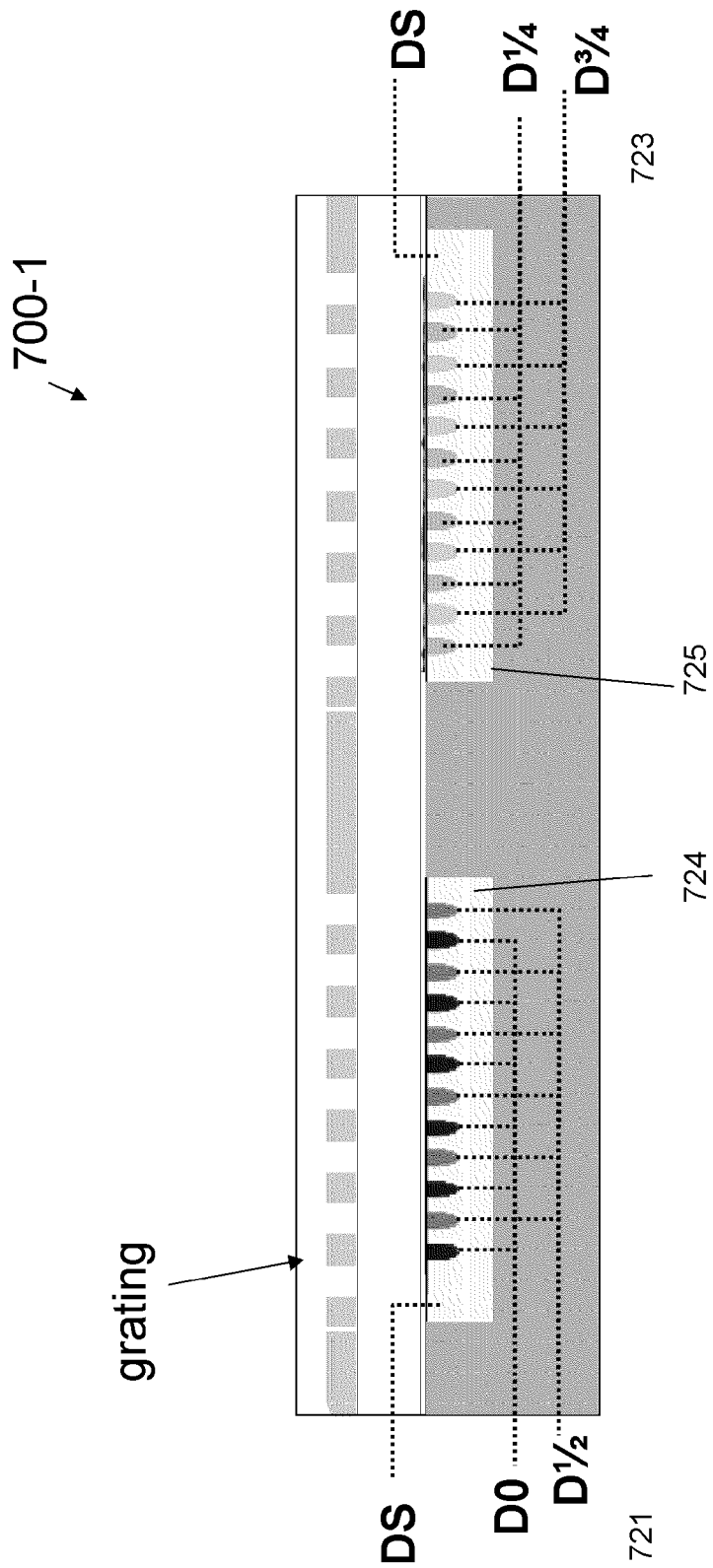
FIG. 21 is a diagrammatic cross sectional view of an image sensor according to an alternative aspect of the invention.

FIG. 21 shows a device embodiment 700-1 similar to that of device 100-1 in FIG. 15, with the exception that the two sets of interleaved diffusion-type diodes 121, 123 (721, 723) are, respectively, disposed in two single, large well-diodes 724, 725. According to this aspect, crosstalk observed in the sub-micron size diffusion-type diodes may be reduced, since the large photodiodes collect the electrons and holes generated by photons that penetrate into the substrate beyond the thin, interleaved diodes. Thus the large well diodes are fabricated deep enough to enclose the interleaved diodes but shallow enough to catch electrons.

Figure 22:
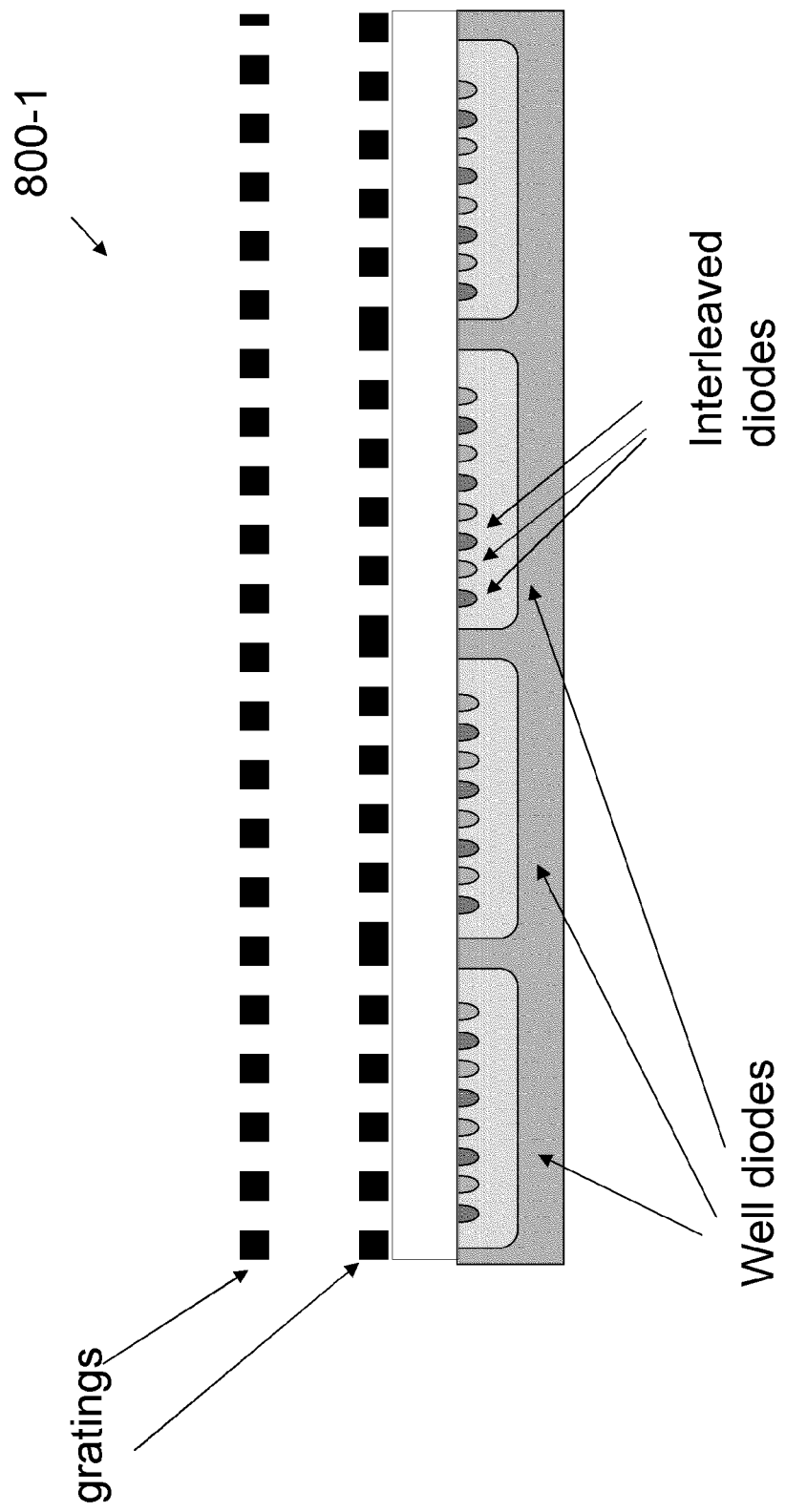
FIG. 22 is a diagrammatic cross sectional view of an image sensor according to an alternative aspect of the invention.

Interleaved/deep-well diodes can also be incorporated into devices which rely on multiple sets of gratings for angle sensitivity. An example device 800-1 using two gratings placed ½ Talbot distance apart vertically and photodiodes at the $1^{st}$ Talbot distance is shown in FIG. 22. As described above, the large-well photodiodes measure the total light flux passing through the two gratings. In this aspect, the mode of operation is identical to that of the basic multiple grating device. However, when the incident angle is such that the light flux through the grating stack is strong, the interleaved photodiodes help locate the lateral offset of the periodic intensity pattern with greater accuracy. This provides improved characterization of incident angle around a set of known angles without interfering with basic function.

Another embodiment of the invention is directed to a method for extracting incident light-angle information from a light source object. The ability to detect said angle information has applications pertaining, but not limited to, sensor networks and sensor arrays; direction and/or speed of motion detection of objects passing over a sensor such as, for example, the direction and speed of a vehicle passing over a sensor embedded in road pavement; detection/reception of multiple data streams from separate transmitters in a free-space optical communication system; bio-medical applications such as, e.g., detection of individual fluorescent cells in tissue containing such fluorescent cells, and others that would be appreciated by persons skilled in the art.

According to a non-limiting aspect, the method may be accomplished entirely without the use of lenses, and performed with image sensors on the physical scale of silicon integrated circuits. For example, a sensor array as described herein above may be positioned adjacent a piece of tissue containing fluorescent cells. Each cell would generate light whose incident angles (into the sensor) would indicate the cell's location in three-dimensional space. By triangulating back from the angles detected by each sensor in the array, as schematically illustrated in FIG. 1*b*, the location of individual fluorescent cells could be detected, as well as changes in their fluorescence independently from the other fluorescent cells.

According to a non-limiting aspect, many image sensor arrays could be deployed as part of a larger array of tissue culture chambers. Each individual image sensor would provide monitoring of its respective sample, providing high-throughput analysis of many samples at once.

According to a non-limiting, alternative aspect, the method may be accomplished using an imaging sensor in combination with a lens system, which may be advantageous to image more distant objects. For example, as shown in FIG. 20*a*, an object 1402 at the focal plane of the lens system 1405 will appear completely in focus on the surface 1406 of the sensor array 1407, and will appear to have an even distribution of angles of incidence 1409. In this case the array acts like a normal CMOS imager. Objects more distant than the focal plane of the lens system will generate blurred images on the array, but the blurring will show a variable set of incident angles that converge on the focal plane of the object, as shown in FIG. 20b. Objects closer than the focal depth of the lens system will also appear blurred, but with a divergent set of incident angles, indicating a focal depth behind the array, as shown in FIG. 20c. Thus the imager can extract useful information that can be used to describe the location of objects both closer and farther away than the optical focal plane of the lens system. In other words, the imager, by detecting incident angle, can extract information about an object region that is thicker than the normal depth of focus associated with a given lens system. Thus this information may be used, e.g., to reconstruct the three-dimensional structure of a scene or, to computationally refocus the image to different focal depths after the image has been captured. The data from such an imager may be used to simultaneously refocus different parts of the image to different depths. And although a single light-emitting object will generate a sensor response that maps to a single incident angle, multiple light sources will result in a linear superposition of responses, each of which depends on the incident angle of each source.

Since the diffraction grating approach to light field imaging described herein is sensitive to the wavelength of light, a given pixel design will work effectively for a limited range of wavelengths. For applications where this wavelength is known in advance, such as in fluorescent microscopy or communication systems using known LEDs, the gratings can be designed appropriately as known in the art. In imaging and/or angle detection applications using white light, a color filter 1430 may be required in conjunction with the chip to limit the incident light wavelengths to the appropriate range. Modern imager processes typically include such color filters; thus they could be incorporated into the basic design. Furthermore, since such processes typically include multiple color filter layers (typically red, green and blue), using these filters in conjunction with three separately tuned sets of gratings (tuned for these different colors) would permit light-field imaging in color.

It is possible to extract three-dimensional information about the source object that is generating the responses of the diodes. Light originating at any given point in space visible to the imager will generate a unique set of responses in the detectors in the imager. In particular, a point at location (x,y,z) will illuminate a point $(x_s, y_s)$ on the imager (defining the plane of the imager as $z_s=0$) with an intensity proportional to $$B_s = \frac{B}{(x-x_s)^2 + (y-y_s)^2 + z^2}$$

with incident angles:

$$\theta_x = \cos^{-1}\left(\frac{z}{\sqrt{(x-x_s)^2 + z^2}}\right)$$

$$\theta_y = \cos^{-1}\left(\frac{z}{\sqrt{(y-y_s)^2 + z^2}}\right)$$

where $\theta_x$ is the azimuth and $\theta_y$ is the altitude. The resulting illumination of individual diodes in that region will follow the equations above, such that, for example, the "zero degree, horizontal" diode will see a brightness of $$D_{0H} = \frac{I_o}{(x-x_s)^2 + (y-y_s)^2 + z^2} \cdot \frac{(1+\cos(k\theta_x))}{2}$$

$$D_{0H} = \frac{I_o}{(x-x_s)^2 + (y-y_s)^2 + z^2} \cdot \frac{\left(1+\cos\left(k\cos^{-1}\left(\frac{z}{\sqrt{(x-x_s)^2+z_2}}\right)\right)\right)}{2}$$

and so on, such that any given diode's response to illumination from a given point in space can be calculated. That is, one can define a response $r(x_s, y_s, a)$ (where $x_s$ and $y_s$ are as above, and a is an index from 1 to 8 representing the phase associated with the diode) to any given stimulus $s(x,y,z)$. This can be rewritten in vector form by giving each diode an index i, (such that each combination $x_s, y_s, a$ has a unique i: for example, for an N×N array with 8 possible angles, $i=a+8 \cdot x_s+N \cdot 8 \cdot y_s$, such that i ranges from 1 to $8N^2$). One can then define an overall response in the array r to a given stimulus point $s(x,y,z)$, where each entry in r is defined as above. If one then calculates this vector for every stimulus location in a volume with dimensions X, Y and Z, (defined as integer multiples of the resolution one wants to image the volume with), one can define a single index, j, for these points in the volume, defined similarly to above. Thus one can define any pattern of light sources in the volume of interest by a second vector s. Since light at each point in s will cause a response in each diode in r, and the effects of each of these light sources will add linearly, one can define a matrix A, where each entry a(i,j) is defined as the response of diode i to a unit light stimulus at point j. It follows that $r=As,$ where r is now a vector of diode responses that captures the total response of the array to a given stimulus pattern in three dimensions.

It is noted that A is not a square matrix, since r has a total of $8N^2$ entries, whereas s has XYZ entries. In most cases where a reasonably high resolution is called for, one can assume that roughly, X=Y=N, and Z is on the order of N as well. Thus one can typically assume that s has many more entries than r (on the order of N/8 times as many).

In order to find s (i.e., the three-dimensional structure of the object being imaged), matrix A is inverted by:

$s=A^{-1}r.$

However, such an inversion is not mathematically possible since A is not square matrix, but is "taller" than it is "wide". There will not be enough information in a planar imager to distinguish all possible structures in a volume being imaged since there are simply more unknowns (the entries in s) than there are equations to define them (the entries in r). Thus a solution to the problem requires that additional constraints be imposed. Two non-limiting examples are discussed below.

EXAMPLE 1

Using Light Field Data For Refocusing And Range Finding

One way to constrain the problem described above is to assume that s is the result of visual information at a particular focal depth, and finding the best estimate for what the image should look like if the detected light originated only in that plane. s now describes a plane with dimensions X×Y, such that s has $X \cdot Y = N^2$ entries. Since this is now actually less than the size of r, A is still not square, but is now "wider" than it is "tall" such that the problem is now-over defined. By using a pseudo-inverse, usually defined for over constrained systems as $(A^TA)^{-1}A^T$, one can extract a best fit for s given r. If there is a reasonably good fit (as there will be if the focal plane chosen is the correct one), then this approach will yield a good approximation of the actual object scene. In particular, if the approximation of s is:

$$s'=p_{inv}(A)r,$$

where $p_{inv}(A)$ is the pseudo-inverse of A, and given that A was chosen such that $$r=As,$$

then by the definition of the pseudo-inverse, the total error |s'−s| is minimized.

This approach can also be applied to data from a normal imager. However, since the mapping between s and r is different, the matrix A will be different, as will as its pseudo-inverse, $p_{inv}(A)$. In particular, the degree to which a pseudo-inverse provides a useful result depends upon the singular values of A (similar to eigenvalues in a square matrix). Moreover, the larger the singular values of a matrix, the less sensitive the inversion process is to small errors and noise. The type of array described here, when used to compute the stimulus s for a given focal plane offset from the plane of the imager, provides a significantly richer description resulting in a matrix with larger singular values. An example of this is shown in FIGS. 15a, b for two 16×16 arrays, one where each pixel simply detects light, and the other where each pixel contains two fingered diodes and a metal grating, such that sets of four pixels form a cell, as shown in FIG. 5c. For a focal plane four pixel widths from the imager plane, the grating based design generates a conversion matrix A whose singular values are consistently larger, by as much as a factor of 100 than those for a normal imager. As a result, calculating the pseudo-inverse for a grating-based imager yields a more accurate, lower noise result than with a normal imager.

A second result of this approach is that one can calculate an error term based upon using the pseudo inverse. In particular, calculating an estimate of r as:

$$r'=As'$$

lets one then find an error term associate with this estimate:

$$err=|r'-r|.$$

If the estimate s' accurately leads to the entries in r, then this error term will be small. This will be true if the source of the image was in fact at the focal depth used when estimating A. On the other hand, if the image originates at some other focal depth, then the estimate will likely be wrong, and the error term will be larger. Simulations confirm this (again for the 16×16 array), with this error term minimized when the actual focal depth is chosen. This is distinct from the case of a normal imager where this error increases monotonically with estimated focal depth regardless of reality (see FIG. 15b). Since this error term can be calculated using only A and r without knowing s a priori, it should be possible to use this error term to recognize the "correct" focal depth when refocusing the image. This information alone can be used for range-finding in a light field independent of the details of the object(s) being imaged.

The method described herein above need not be applied to the entire image, but can be applied to subsections of the image such that they can be refocused independently and/or their range found, leading to better overall focus and/or a range map across the image.

EXAMPLE II

Using Light Field Data For Extraction Of Sparse Fluorescent Sources

Another exemplary application pertains to imaging the three dimensional structure of fluorescing cells in tissue. Since the goal of such an application would be to be able to independently quantify the fluorescence of multiple cells at different focal planes, refocusing is not an appropriate approach. However, if one adds the two additional constraints: i) that all entries in s must be strictly positive (there is no such thing as negative fluorescence), and ii) that the fluorescent sources are relatively sparsely distributed in the volume being imaged, one may assume that the number of fluorescent cells is smaller than $N^2$, the number of pixels. If this holds true, then one can find each of these sources iteratively and in order of brightness as follows:

a) correlate r with the expected response to each possible entry in s as:

$$c=rA^T;$$

b) find the index, j, of s that correlates best with r (index of the maximum entry in c);

c) estimate the maximum value of s at this index that would yield a response r' such that r(i)'<r(i) for all indices i. This implies that r(i)−gA(j,i)>0, where A(i,j) is the $i^{th}$ entry of the $j^{th}$ column Therefore g=min(r(i)/A(j,i)) across all values of i;

d) reduce by a factor $\lambda$, where $0<\lambda<1$ and add to the existing estimate of s $$s'(j)=s'(j)+\lambda g;$$

e) update residual value of r:

$$r=r-As';$$

f) repeat steps (a-e).

Each iteration of this algorithm finds the most likely dominant point source of the light field seen in r, includes that source in the estimate of the stimulus, s', then removes that portion of the effect from r permitting the algorithm to find the next most dominant source. $\lambda$ is chosen to be <1 so that no entry of r is driven to zero prematurely. In a simulation that provided reasonable results, $\lambda=0.5$.

The various embodiments described herein are compatible with a variety of integrated light detectors/sensors including, without limitation, reverse-biased p-n junction diodes, forward bias diodes (i.e., photovoltaics), p-i-n diodes, charge-coupled devices (CCDs), and single-photon avalanche diodes.

The use of the terms "a" and "an" and "the" and similar references in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening.

The recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not impose a limitation on the scope of the invention unless otherwise claimed.

No language in the specification should be construed as indicating any non-claimed element as essential to the practice of the invention.

It will be apparent to those skilled in the art that various modifications and variations can be made to the present invention without departing from the spirit and scope of the invention. There is no intention to limit the invention to the specific form or forms disclosed, but on the contrary, the intention is to cover all modifications, alternative constructions, and equivalents falling within the spirit and scope of the invention, as defined in the appended claims. Thus, it is intended that the present invention cover the modifications and variations of this invention provided they come within the scope of the appended claims and their equivalents.

We claim:

1. A lens-less, angle-sensitive pixel (ASP) device, comprising:
   a device support structure;
   a first periodic, light diffracting structure having a period, $p_1$, disposed in or on a top surface of the support structure;
   a second periodic structure having a period, $p_2$, oriented parallel to the first periodic, light diffracting structure and disposed in the support structure at a selected distance below the first periodic light diffracting structure; and
   a sensor disposed in the support structure below the second periodic structure, where $p_1$ is equal to or greater than $\lambda$, which is the wavelength of a monochromatic, plane, incident wavefront on the first periodic, light diffracting structure.

2. The device of claim 1, wherein $p_2 = p_1$.

3. The device of claim 1, wherein the second periodic structure is disposed in the support structure at a second selected Talbot distance, $z_{T2} = (m_2/n_2)(2p_1^2/\lambda)$, where m, n are positive integers and $p_1$ is equal to or greater than $\lambda$.

4. The device of claim 1, wherein the sensor is disposed in the support structure at a first selected Talbot distance, $z_{T1} = (m_1/n_1)(2p_1^2/\lambda)$, below the first periodic, light diffracting structure and the second periodic structure, where m, n are positive integers and $p_1$ is equal to or greater than $\lambda$.

5. The device of claim 4, wherein the sensor comprises at least two sets of periodic, interleaved diffusion-type diodes, further wherein the sets of diodes are, respectively, laterally displaced from the first periodic, light diffracting structure by a distance $np_1/m$, where n can have the values 0, 1, 2, 3, 4, 5, 6, 7, 8 and m can have the values 2, 3, 4, 8.

6. The device of claim 1, wherein the sensor is a single-well p-n photodiode.

7. The device of claim 5, wherein the sensor further comprises at least two sets of periodic, interleaved diffusion-type diodes, disposed at a depth $z_{T1} = (m_1/n_1)(2p_1^2/\lambda)$, further wherein the sets of diodes are, respectively, laterally displaced from the first periodic, light diffracting structure by a distance $np_1/m$, where n can have the values 0, 1, 2, 3, 4, 5, 6, 7, 8 and m can have the values 2, 3, 4, 8, further wherein the sets of diodes are disposed in the single-well p-n photodiode.

8. The device of claim 1, wherein the first periodic, light diffracting structure is a Ronchi ruling.

9. The device of claim 1, wherein the device is an integrated CMOS semiconductor structure.

10. A lens-less light-field detector, comprising:
    a detector support structure;
    a first pixel device, comprising:
      a first periodic, light diffracting structure having a period, $p_1$, disposed in or on a top surface of the support structure;
      a second periodic structure having a period, $p_2$, oriented parallel to the first periodic, light diffracting structure and disposed in the support structure at a second selected Talbot distance, $z_{T2} = (m_2/n_2)(2p_1^2/\lambda)$, below the first periodic light diffracting structure,
    wherein the second periodic structure is not laterally displaced from the first periodic, light diffracting structure; and
      a first sensor disposed in the support structure at a selected distance below the second periodic structure,
    further wherein m, n are positive integers, $\lambda$ is the wavelength of an monochromatic, plane, incident wavefront on the first periodic, light diffracting structure, $p_1$ is equal to or greater than $\lambda$; and
    a second pixel device disposed linearly adjacent the first pixel device, comprising:
      a first periodic, light diffracting structure having a period, $p_1$, disposed in or on a top surface of the support structure;
      a second periodic structure having a period, $p_2$, oriented parallel to the first periodic, light diffracting structure and disposed in the support structure at the second selected Talbot distance below the first periodic, light diffracting structure,
    wherein the second periodic structure is laterally displaced from the first periodic, light diffracting structure by an amount $(m_2/n_2)p_1$; and
      a second sensor disposed in the support structure below the second periodic structure.

11. The detector of claim 10, wherein the first sensor is disposed in the support structure at a first selected Talbot distance, $z_{T1} = (m_1/n_1)(2p_1^2/\lambda)$, below the first periodic, light diffracting structure, further wherein $z_{T2}$ is less than $z_{T1}$.

12. The detector of claim 10, wherein $p_2 = p_1$.

13. The detector of claim 10, wherein the first and second sensors are each a single-well p-n photodiode.

14. The detector of claim 13, wherein each of the first and second sensors further comprise at least two sets of periodic, interleaved diffusion-type diodes, disposed at a depth $z_{T1} = (m_1/n_1)(2p_1^2\lambda)$, further wherein the sets of diodes are, respectively, laterally displaced from the first periodic, light diffracting structure by a distance $np_1/m$, where n can have the values 0, 1, 2, 3, 4, 5, 6, 7, 8 and m can have the values 2, 3, 4, 8,
further wherein each of the sets of diodes are disposed, respectively, in each of the single-well p-n photodiodes.

15. The detector of claim 13, further comprising at least two sets of periodic, interleaved diffusion-type diodes disposed in each of the first and second single-well p-n photodiodes.

16. The detector of claim 10, wherein each of the first and second sensors further comprise at least two sets of periodic, interleaved diffusion-type diodes disposed at a depth $z_{T1} = (m_1/n_1)(2p_1^2/\lambda)$, below the first periodic, light diffracting structure where $z_{T2} < z_{T1}$, further wherein the sets of diodes are, respectively, laterally displaced from the first periodic, light diffracting structure by a distance $np_1/m$, where n can have the values 0, 1, 2, 3, 4, 5, 6, 7, 8 and m can have the values 2, 3, 4, 8.

17. The detector of claim 10, further comprising:
at least an $n^{th}$ ($n \geq 3$) pixel device disposed linearly adjacent the ($n^{th}-1$) pixel device, comprising:
a first periodic, light diffracting structure having a period, $p_1$, disposed in or on a top surface of the support structure;
a second periodic structure having a period, $p_2$, oriented parallel to the first periodic, light diffracting structure and disposed in the support structure below the first periodic, light diffracting structure,
wherein the second periodic, light diffracting structure is laterally displaced from the first periodic, light diffracting structure by an amount $(m_n/n_n)p_1$, where $(m_n/n_n)>(m_{n-1}/n_{n-1})$; and
an $n^{th}$ sensor disposed in the support structure at the first selected Talbot distance below the first periodic, light diffracting structure.

18. The detector of claim 17, wherein the $n^{th}$ sensor is a single-well p-n photodiode.

19. The detector of claim 17, wherein the $n^{th}$ sensor further comprises at least two sets of periodic, interleaved diffusion-type diodes, disposed at a depth $z_{T1}=(m_1/n_1)(2p_1^2/\lambda)$, further wherein the sets of diodes are, respectively, laterally displaced from the first periodic, light diffracting structure by a distance $np_1/m$, where n can have the values 0, 1, 2, 3, 4, 5, 6, 7, 8 and m can have the values 2, 3, 4, 8.

20. The detector of claim 18, further comprising at least two sets of periodic, interleaved diffusion-type diodes disposed in each of the $n^{th}$ single-well p-n photodiodes.

21. The detector of claim 17, wherein the $n^{th}$ sensor further comprises at least two sets of periodic, interleaved diffusion-type diodes disposed at a depth $z_{T1}=(m_1/n_1)(2p_1^2/\lambda)$, below the first periodic, light diffracting structure, where $z_{T2}<z_{T1}$, further wherein the sets of diodes are, respectively, laterally displaced from the first periodic, light diffracting structure by a distance $np_1/m$, where n can have the values 0, 1, 2, 3, 4, 5, 6, 7, 8 and m can have the values 2, 3, 4, 8, further wherein each of the sets of diodes are disposed, respectively, in each of the $n^{th}$ single-well p-n photodiodes.

22. The detector of claim 16, wherein every $n^{th}$ ($n \geq 3$) pixel device further comprises:
a first intermediate periodic, light diffracting structure having a period, $p_1$, disposed between the first periodic structure and the second periodic structure, oriented perpendicularly to the first and second periodic structures; and
a second intermediate periodic, light diffracting structure having a period, $p_2$, disposed between the second periodic structure and the $n^{th}$ sensors, oriented perpendicularly to the first and second periodic structures,
wherein in every $n^{th}$ ($n \geq 3$) pixel device, the first and second intermediate periodic, light diffracting structures are laterally displaced from the first periodic structure by an amount $(m_n/n_n)p_1$, where $(m_n/n_n) (m_{n-1}/n_{n-1})$.

23. A lens-less light field imaging device comprising a two-dimensional, M×N array of light-field detectors as set forth in claim 17.

24. The detector of claim 10, wherein the first and second pixel devices further comprise:
a first intermediate periodic, light diffracting structure having a period, $p_1$, disposed between the first periodic, light diffracting structure and the second periodic structure, oriented perpendicularly to the first and second periodic structures; and
a second intermediate periodic, light diffracting structure having a period, $p_2$, disposed between the second periodic structure and the first and second sensors, oriented perpendicularly to the first and second periodic structures,
wherein in the first pixel device, the first and second intermediate periodic, light diffracting structures are not laterally displaced from the respective first and second periodic structure, further wherein in the second pixel device, the first and second intermediate periodic, light diffracting structures are laterally displaced from the respective first and second periodic structures by an amount $(m_2/n_2)p_1$.

25. The detector of claim 24, wherein $p_2=p_1$.

26. A lens-less light field imaging device comprising a two-dimensional, M×N array of light-field detectors as set forth in claim 10.

27. A pixel device, comprising:
a device support structure;
a first periodic, light diffracting structure having a period, $p_1$, disposed in or on a top surface of the support structure;
a second periodic structure having a period, $p_2$, oriented parallel to the first periodic structure disposed in the support structure at a selected Talbot distance, $z_T=(m/n)(2p_1^2/\lambda)$ below the first periodic, light diffracting structure,
where m, n are positive integers, $\lambda$ is the wavelength of an monochromatic, plane, incident wavefront on the first periodic, light diffracting structure, and $p_1$ is equal to or greater than $\lambda$.

28. The device of claim 27, wherein the second periodic structure further comprises at least two sets of interleaved diffusion-type diodes, further wherein the sets of diodes are, respectively, laterally displaced from the first periodic, light diffracting structure by a distance $np_1/m$, where n can have the values 0, 1, 2, 3, 4, 5, 6, 7, 8 and m can have the values 2, 3, 4, 8.

29. A method for determining a direction of incident light from an object, comprising:
creating a periodic, interference pattern of the incident light from the object;
detecting the interference pattern; and;
determining a phase shift of the pattern relative to a reference position.

* * * * *

UNITED STATES PATENT AND TRADEMARK OFFICE
CERTIFICATE OF CORRECTION

PATENT NO. : 8,530,811 B2
APPLICATION NO. : 13/055566
DATED : September 10, 2013
INVENTOR(S) : Alyosha Molnar and Albert Wang It is certified that error appears in the above-identified patent and that said Letters Patent is hereby corrected as shown below:

In the Claims
Column 20, claim 10, line 20, the word "an" should be "a." At column 21, claim 22, line 55, the symbol ">" should be entered between (mn/nn) (mn-1/nn-1), so it will appear as "(mn/nn) > (mn-1/nn-1)." At column 22, claim 27, line 36, the word "an" should be "a."

Signed and Sealed this
Eleventh Day of March, 2014

Michelle K. Lee
*Deputy Director of the United States Patent and Trademark Office*